United States Patent
Olsen

(10) Patent No.: US 10,524,738 B2
(45) Date of Patent: Jan. 7, 2020

(54) NONINVASIVE SENSOR SYSTEM WITH VISUAL INFOGRAPHIC DISPLAY

(71) Applicant: Cercacor Laboratories, Inc., Irvine, CA (US)

(72) Inventor: Gregory A. Olsen, Trabuco Canyon, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 255 days.

(21) Appl. No.: 15/146,810

(22) Filed: May 4, 2016

(65) Prior Publication Data

US 2016/0324488 A1 Nov. 10, 2016

Related U.S. Application Data

(60) Provisional application No. 62/156,551, filed on May 4, 2015, provisional application No. 62/156,722, filed
(Continued)

(51) Int. Cl.
*A61B 5/02* (2006.01)
*A61B 5/00* (2006.01)
(Continued)

(52) U.S. Cl.
CPC .......... *A61B 5/7425* (2013.01); *A61B 5/0205* (2013.01); *A61B 5/02438* (2013.01);
(Continued)

(58) Field of Classification Search
CPC . A61B 5/0205; A61B 5/02438; A61B 5/1455; A61B 5/742; A61B 5/7425;
(Continued)

(56) References Cited

U.S. PATENT DOCUMENTS 4,960,128 A 10/1990 Gordon et al.
4,964,408 A 10/1990 Hink et al.
(Continued)

OTHER PUBLICATIONS

US 8,845,543 B2, 09/2014, Diab et al. (withdrawn)

*Primary Examiner* — Eric D. Bertram
(74) *Attorney, Agent, or Firm* — Knobbe, Martens, Olson & Bear, LLP

(57) ABSTRACT

A sensor system for obtaining and displaying information relating to physiological parameters, such as Total Hemoglobin and Pulse rate for use by a user such as an athlete. The system can present the measured physiological parameters to the user in a useful way. For example the system can display a visual multi quadrant infographic display, which can present the total hemoglobin values measured by the system in a particular season. The system can also display a visual elevation infographic display, which can present a comparison of the total hemoglobin values measured by the system over a period of time and/or at various altitudes. The system can also display a visual yin-yang infographic display, which can present a comparison of one or more metrics calculated by the system or one or more parameters measured by the system. The system can provide useful information about the user's health and/or well-being and allow the user to quickly and easily view and interpret relevant information.

10 Claims, 12 Drawing Sheets

Related U.S. Application Data on May 4, 2015, provisional application No. 62/156,581, filed on May 4, 2015.

(51) Int. Cl.
| | |
|---|---|
| *A61B 5/0205* | (2006.01) |
| *A61B 5/145* | (2006.01) |
| *A61B 5/1455* | (2006.01) |
| *A61B 5/024* | (2006.01) |
| *G16H 15/00* | (2018.01) |
| *A61B 5/0255* | (2006.01) |

(52) U.S. Cl.
CPC ........ *A61B 5/1455* (2013.01); *A61B 5/14546* (2013.01); *A61B 5/14552* (2013.01); *A61B 5/7275* (2013.01); *A61B 5/743* (2013.01); *A61B 5/7475* (2013.01); *G16H 15/00* (2018.01); *A61B 5/0255* (2013.01)

(58) Field of Classification Search
CPC ..... A61B 5/743; A61B 5/7435; A61B 5/7475; A63B 71/0619
See application file for complete search history.

(56) References Cited

U.S. PATENT DOCUMENTS

| | | | |
|---|---|---|---|
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |

(56) References Cited

U.S. PATENT DOCUMENTS

| | | |
|---|---|---|
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |

(56) References Cited

U.S. PATENT DOCUMENTS

| | | |
|---|---|---|
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |

(56) References Cited

U.S. PATENT DOCUMENTS

| | | |
|---|---|---|
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |

(56) References Cited

U.S. PATENT DOCUMENTS

| | | |
|---|---|---|
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| D833,624 S | 11/2018 | DeJong et al. |
| 10,123,726 B2 | 11/2018 | Al-Ali et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Al-Ali et al. |
| 10,188,348 B2 | 1/2019 | Kiani et al. |
| RE47,218 E | 2/2019 | Ali-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,305,775 B2 | 5/2019 | Lamego et al. |
| 10,307,111 B2 | 6/2019 | Muhsin et al. |
| 2004/0206353 A1* | 10/2004 | Conroy, Jr. ........ A61B 5/14551 128/204.23 |
| 2006/0161054 A1 | 7/2006 | Reuss et al. |
| 2007/0271009 A1* | 11/2007 | Conroy, Jr. ............ B64D 13/00 701/10 |
| 2007/0282478 A1 | 12/2007 | Al-Ali et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0110416 A1* | 5/2010 | Barrett ............... A61B 5/14535 356/40 |
| 2010/0298675 A1* | 11/2010 | Al-Ali ................ A61B 5/14551 600/322 |
| 2011/0001605 A1 | 1/2011 | Kiani et al. |
| 2011/0082711 A1 | 4/2011 | Poeze et al. |
| 2011/0105854 A1 | 5/2011 | Kiani et al. |
| 2011/0125060 A1 | 5/2011 | Telfort et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2012/0059267 A1 | 3/2012 | Lamego et al. |
| 2012/0123231 A1* | 5/2012 | O'Reilly ............... A61B 5/0261 600/340 |
| 2012/0136582 A1* | 5/2012 | Barrett ............... A61B 5/14535 702/19 |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0190581 A1 | 7/2013 | Al-Ali et al. |
| 2013/0197328 A1 | 8/2013 | Diab et al. |
| 2013/0211214 A1* | 8/2013 | Olsen .................... A61B 5/742 600/316 |
| 2013/0243021 A1 | 9/2013 | Siskavich |
| 2013/0253334 A1 | 9/2013 | Al-Ali et al. |
| 2013/0267793 A1* | 10/2013 | Meador ............... A61B 5/0205 600/301 |
| 2013/0296672 A1 | 11/2013 | O'Neil et al. |
| 2013/0296713 A1 | 11/2013 | Al-Ali et al. |
| 2013/0317370 A1 | 11/2013 | Dalvi et al. |

(56) References Cited

U.S. PATENT DOCUMENTS

| | | |
|---|---|---|
| 2013/0324808 A1 | 12/2013 | Al-Ali et al. |
| 2013/0331660 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0034353 A1 | 2/2014 | Al-Ali et al. |
| 2014/0051953 A1 | 2/2014 | Lamego et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0206962 A1* | 7/2014 | Tanii ................ A61B 5/0059 600/322 |
| 2014/0206963 A1 | 7/2014 | Al-Ali |
| 2014/0213864 A1 | 7/2014 | Abdul-Hafiz et al. |
| 2014/0236491 A1* | 8/2014 | Katayev .............. G16H 50/70 702/19 |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0303520 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0032029 A1 | 1/2015 | Al-Ali et al. |
| 2015/0038859 A1 | 2/2015 | Dalvi et al. |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |

(56) References Cited

U.S. PATENT DOCUMENTS

| | | |
|---|---|---|
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0038143 A1 | 2/2019 | Al-Ali |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150800 A1 | 5/2019 | Poeze et al. |
| 2019/0150856 A1 | 5/2019 | Kiani et al. |
| 2019/0167161 A1 | 6/2019 | Al-Ali et al. |

\* cited by examiner

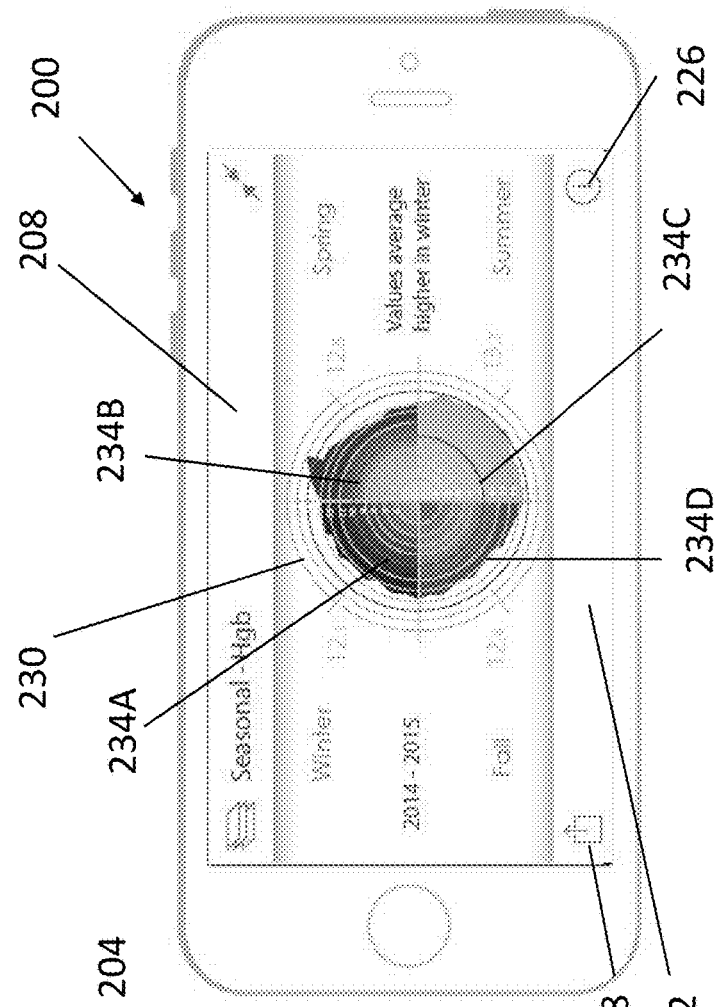
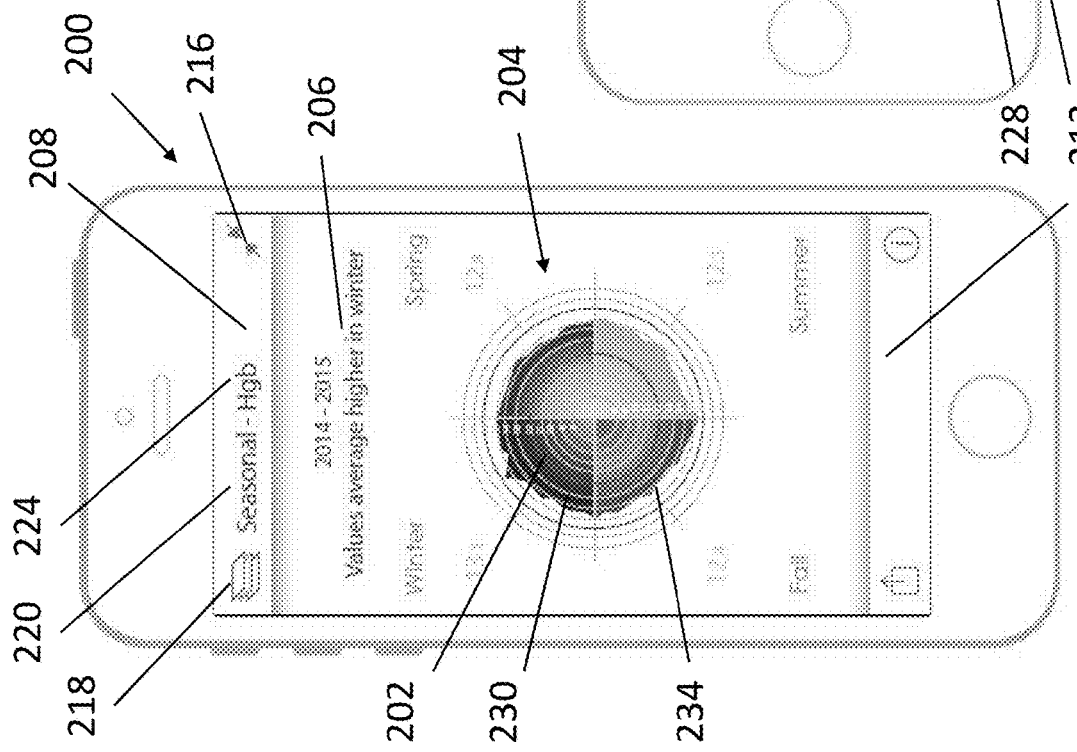
Figure 2A
Figure 2B

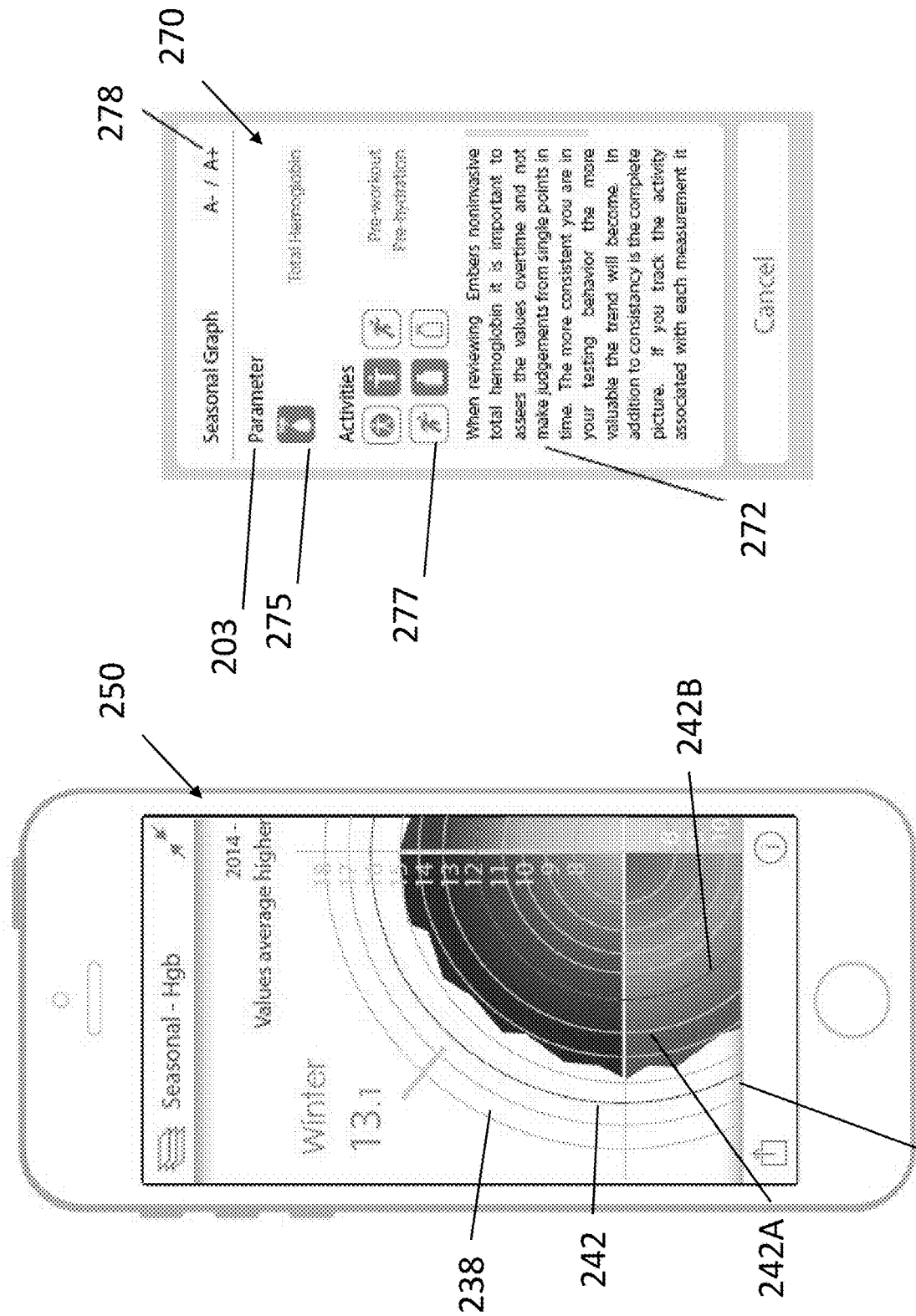

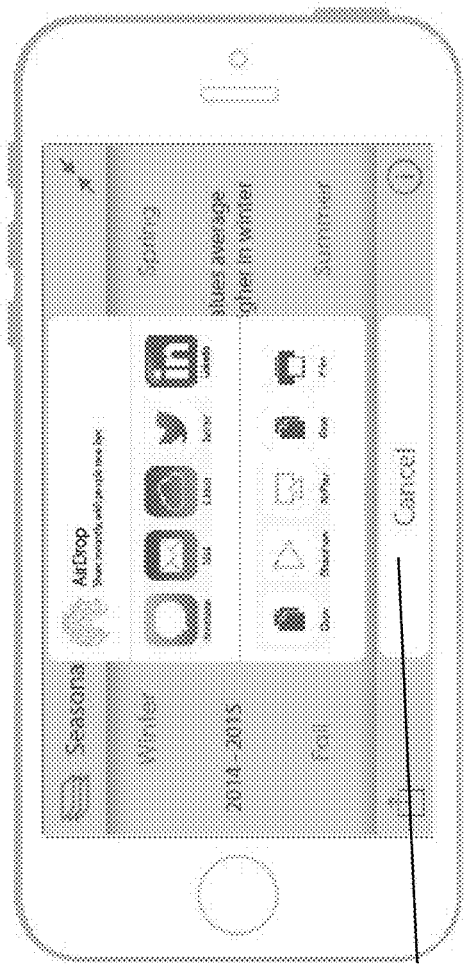
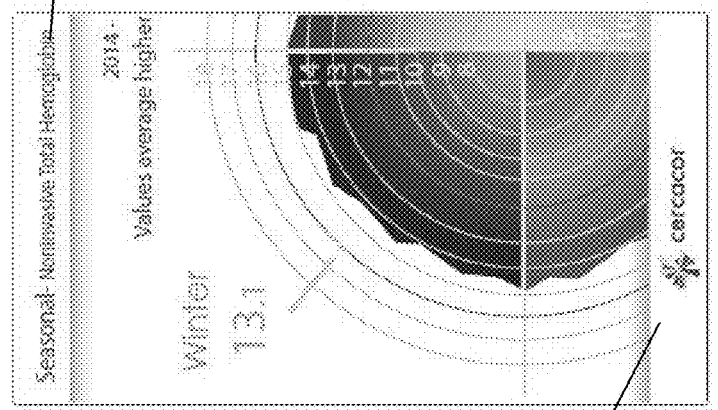
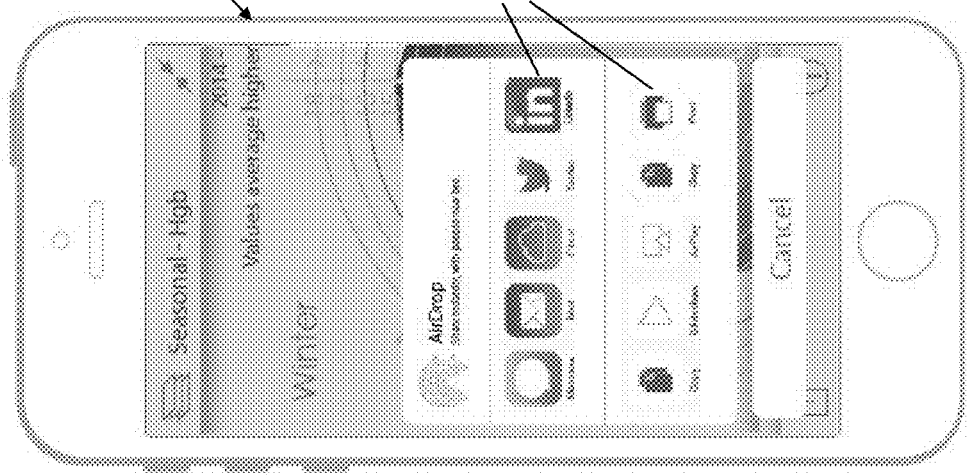

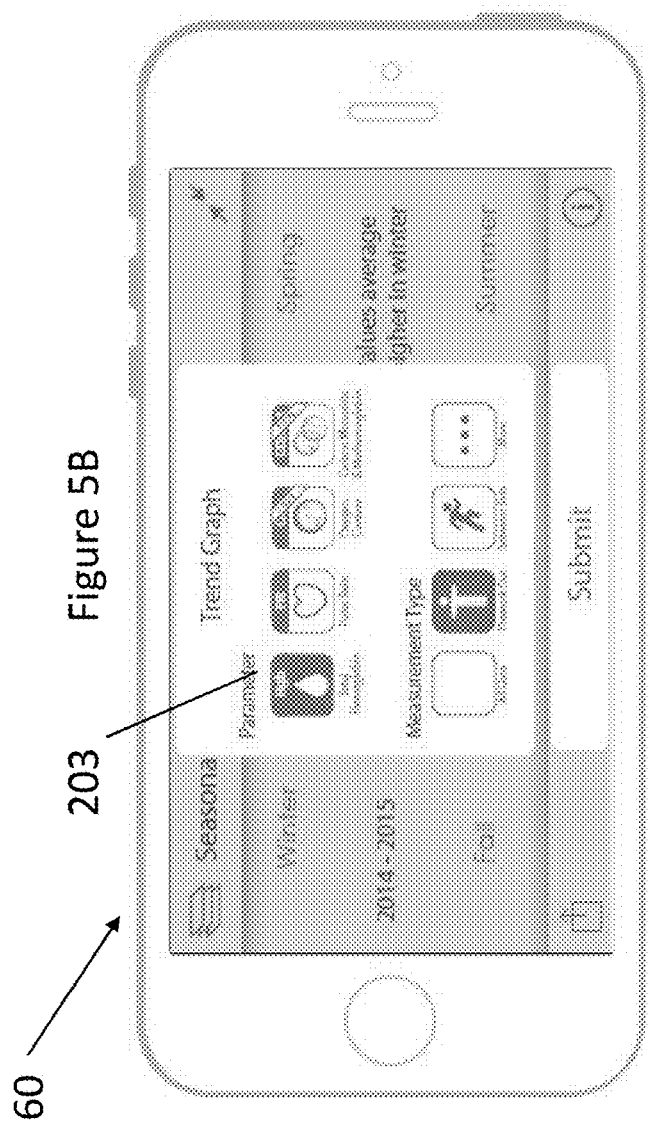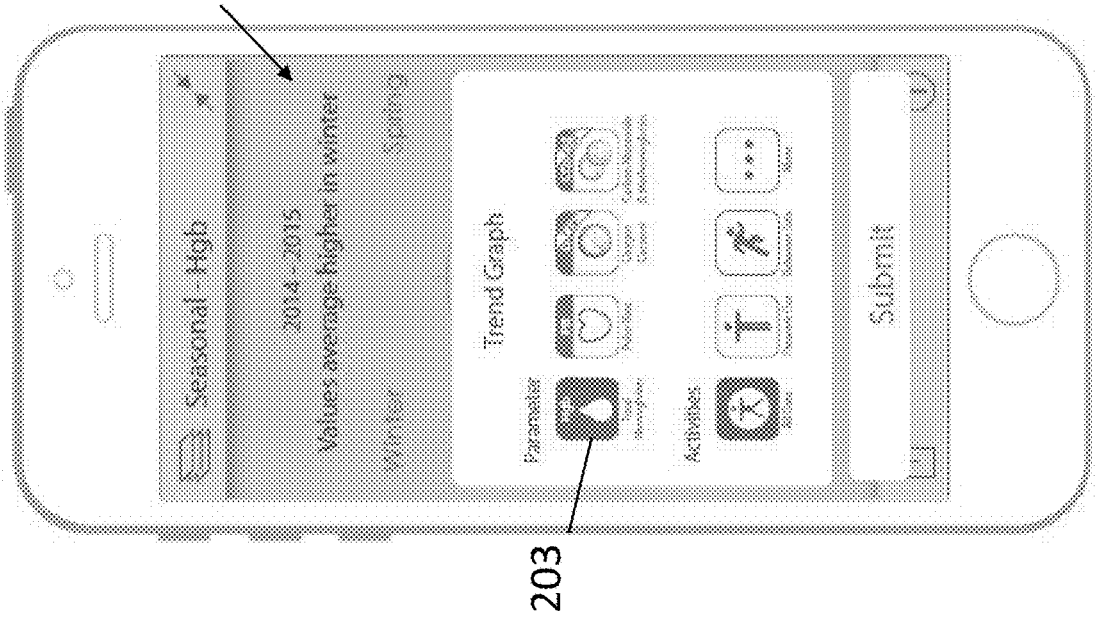
Figure 5B
Figure 5A

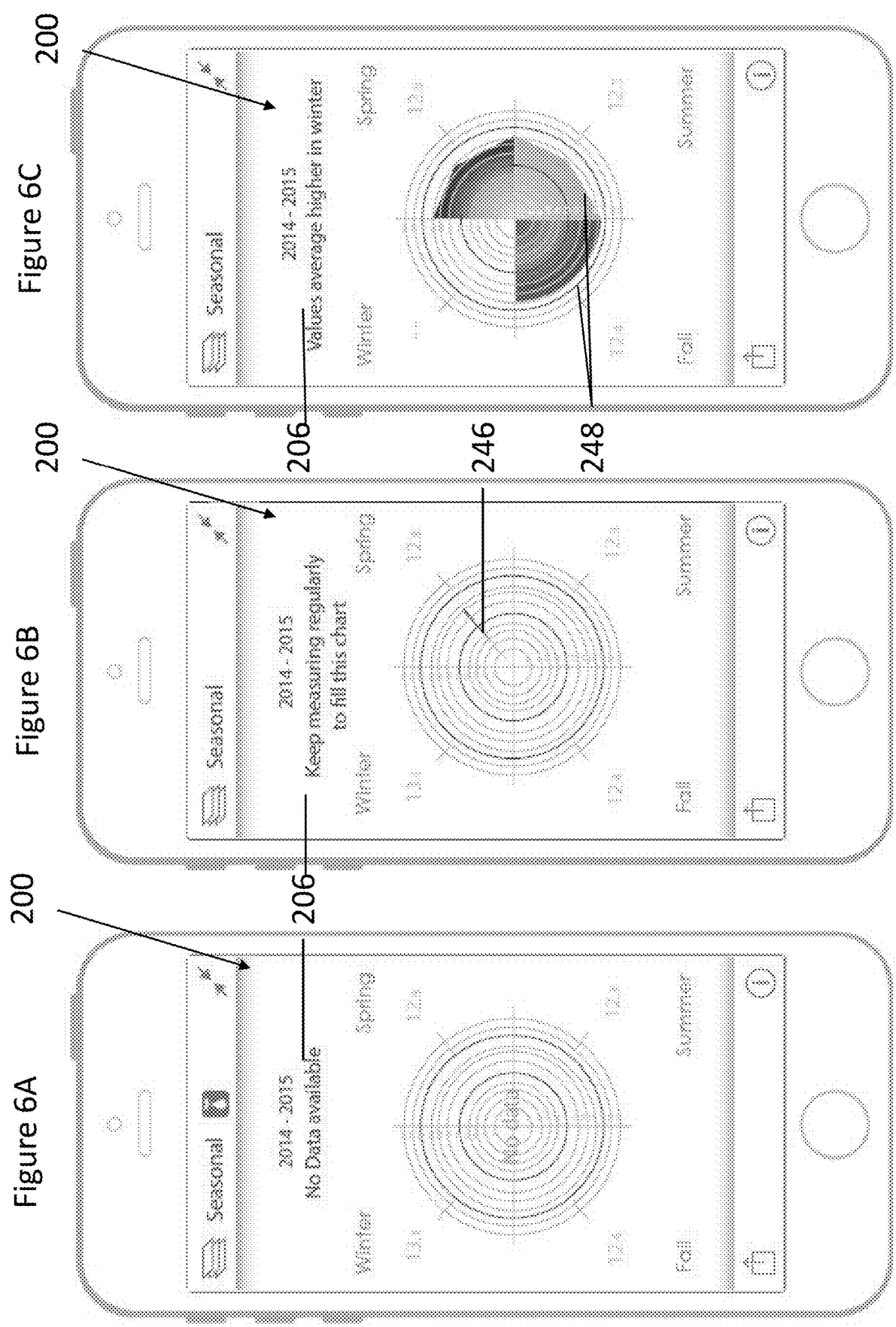

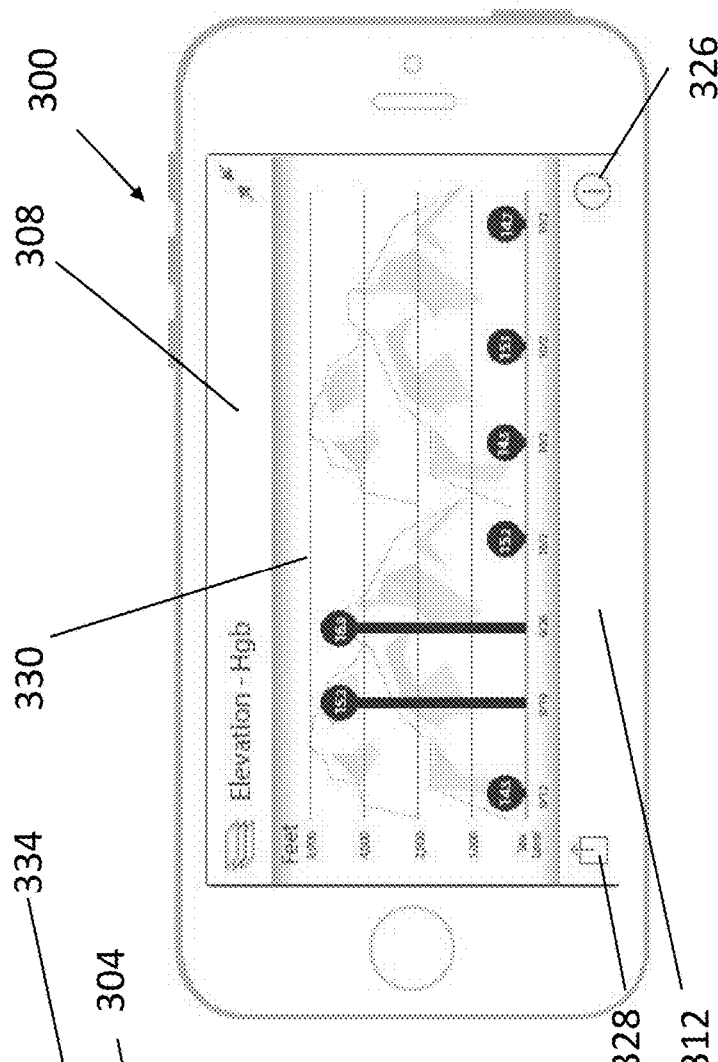
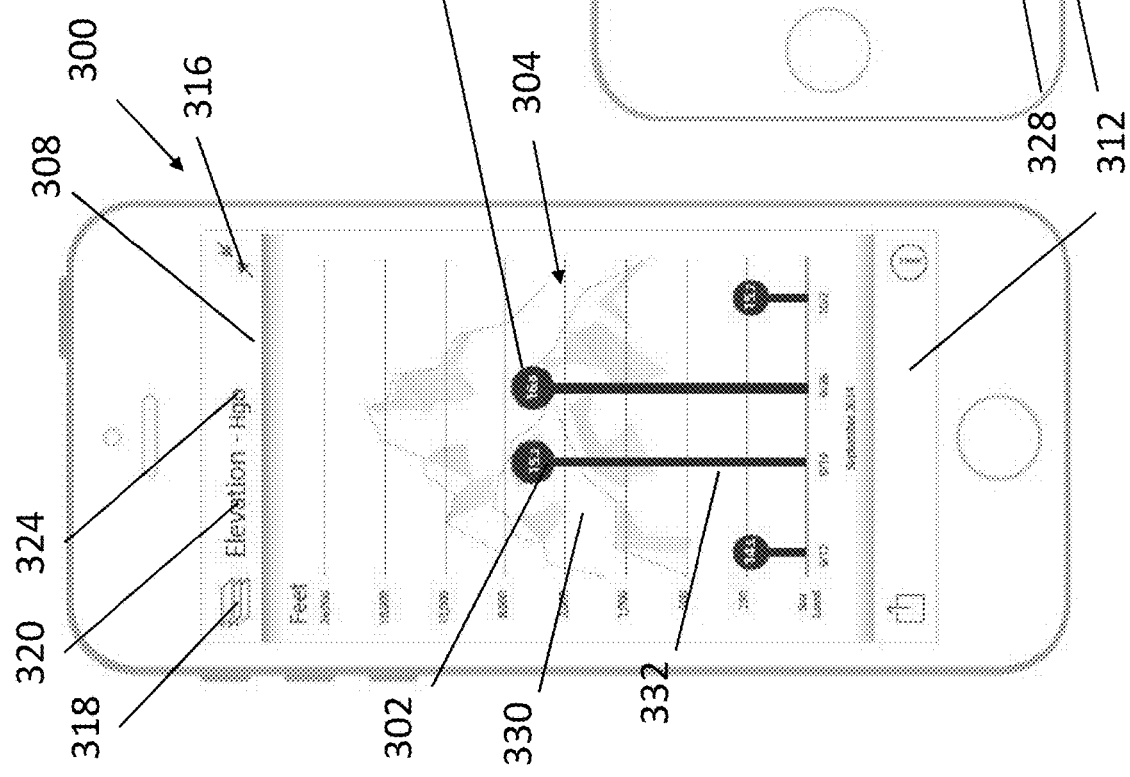
Figure 7A
Figure 7B

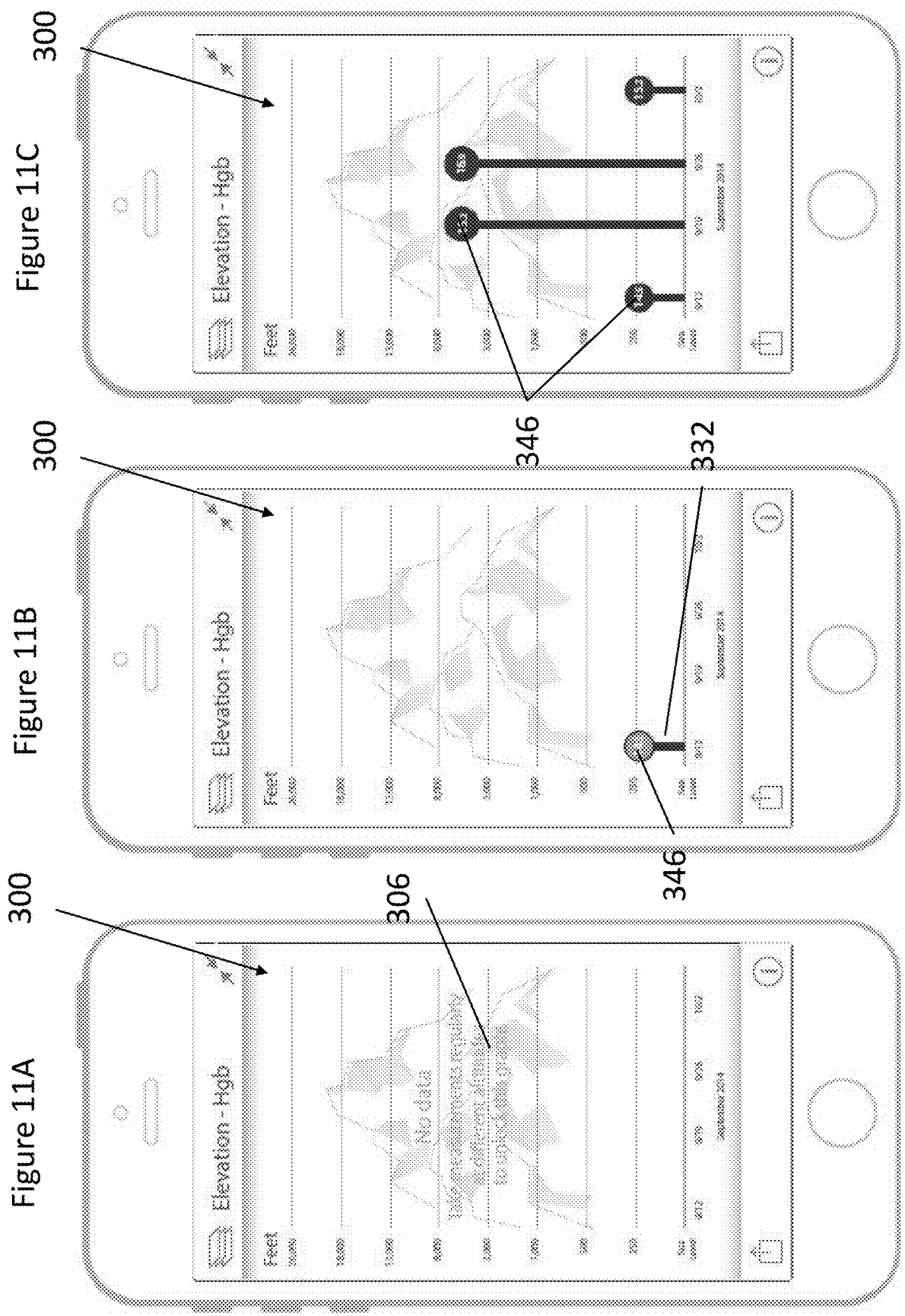

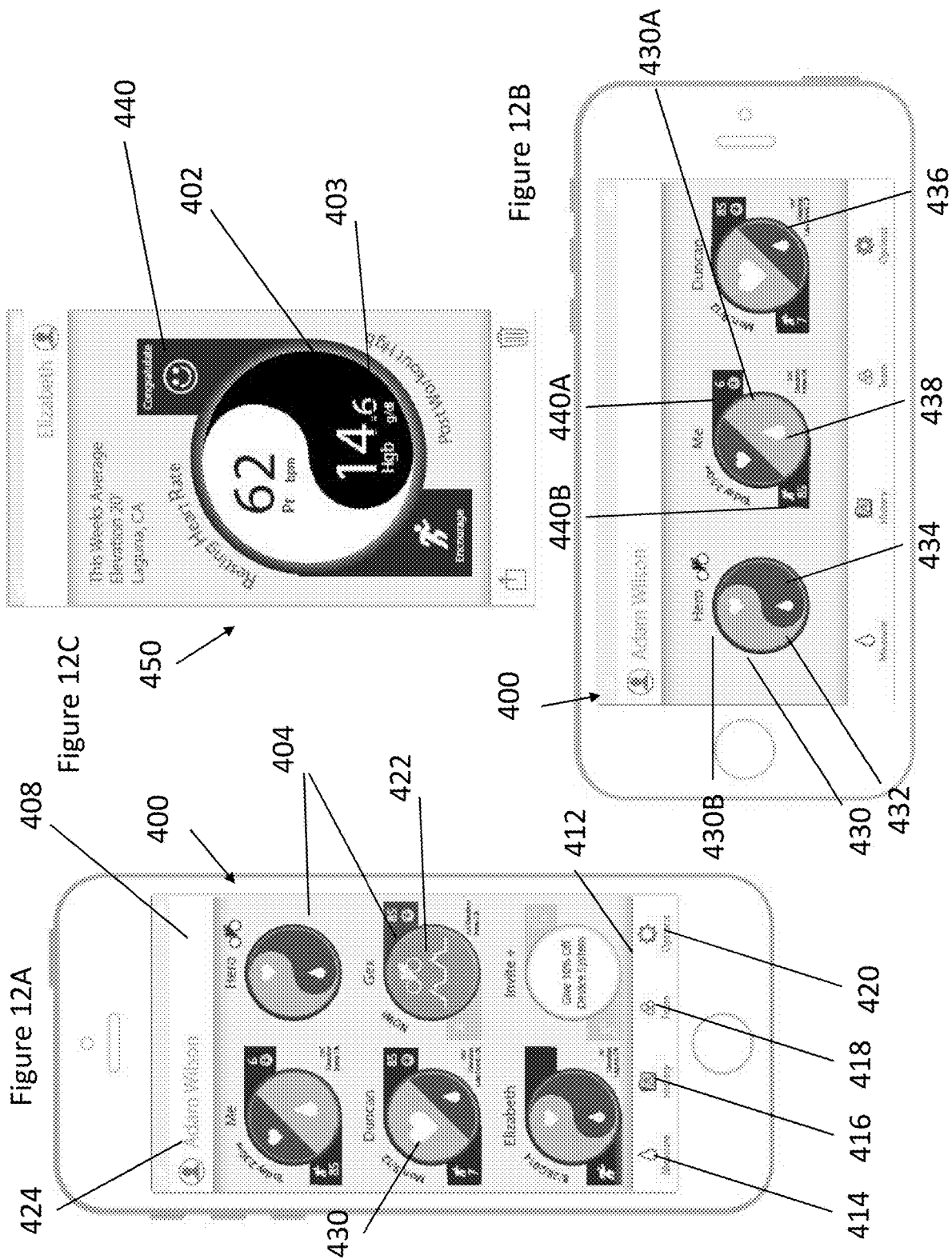

NONINVASIVE SENSOR SYSTEM WITH VISUAL INFOGRAPHIC DISPLAY

RELATED APPLICATIONS

This application is non-provisional of U.S. Provisional Application No. 62/156,581, filed May 4, 2015, U.S. Provisional Application No. 62/156,722, filed May 4, 2015, and U.S. Provisional Application No. 62/156,551, filed May 4, 2015, the disclosure of which is hereby incorporated by reference.

BACKGROUND OF THE INVENTION

User monitoring devices generally include sensors, processing equipment, and displays for obtaining and analyzing a medical patient's physiological parameters. Physiological parameters include, for example, respiratory rate, SpO2 level, pulse rate, total hemoglobin (tHb), oxygen content, carbon monoxide and methemoglobin content, and blood pressure, among others. Users can use the physiological parameters obtained from the user to determine an overall health, wellness, and/or fitness of the user. Users can use the physiological parameters to determine and make adjustments in a diet and/or exercise routine to enhance athletic performance.

User monitors capable of measuring pulse oximetry parameters, such as SpO2 and pulse rate in addition to advanced parameters, such as HbCO, HbMet and total hemoglobin (Hbt, THb, or SpHb) and corresponding multiple wavelength optical sensors are described in at least U.S. patent application Ser. No. 11/367,013, filed Mar. 1, 2006 and entitled Multiple Wavelength Sensor Emitters and U.S. patent application Ser. No. 11/366,208, filed Mar. 1, 2006 and entitled Noninvasive Multi-Parameter Patient Monitor, both assigned to Cercacor Laboratories of Irvine, Calif. (Cercacor) and both incorporated by reference herein. Further, noninvasive blood parameter monitors and corresponding multiple wavelength optical sensors, such as Rainbow™ adhesive and reusable sensors and RAD-57™ and Radical-7™ monitors for measuring SpO2, pulse rate, perfusion index, signal quality, HbCO, and HbMet among other parameters are also available from Masimo Corporation, Irvine, Calif. (Masimo).

Advanced physiological monitoring systems may incorporate pulse oximetry in addition to advanced features for the calculation and display of other blood parameters, such as carboxyhemoglobin (HbCO), methemoglobin (HbMet) and total hemoglobin (Hbt or SpHb), as a few examples. Advanced physiological monitors and corresponding multiple wavelength optical sensors capable of measuring parameters in addition to SpO2, such as HbCO, HbMet and Hbt are described in at least U.S. patent application Ser. No. 11/367,013, filed Mar. 1, 2006, titled Multiple Wavelength Sensor Emitters and U.S. patent application Ser. No. 11/366,208, filed Mar. 1, 2006, titled Noninvasive Multi-Parameter Patient Monitor, which are each hereby incorporated by reference herein in their entirety. Further, noninvasive blood parameter monitors and corresponding multiple wavelength optical sensors, such as Rainbow™ adhesive and reusable sensors and RAD-57™ and Radical-7™ monitors for measuring SpO2, pulse rate, perfusion index (PI), signal quality (SiQ), pulse variability index (PVI), HbCO and HbMet among other parameters are also available from Masimo.

SUMMARY

For purposes of summarizing the disclosure, certain aspects, advantages and novel features of several embodiments have been described herein. It is to be understood that not necessarily all such advantages can be achieved in accordance with any particular embodiment of the embodiments disclosed herein. Thus, the embodiments disclosed herein can be embodied or carried out in a manner that achieves or optimizes one advantage or group of advantages as taught herein without necessarily achieving other advantages as can be taught or suggested herein.

According to some embodiments, a sports training infographic method for presenting user data in a useful way for user use can include obtaining, by at least one sensor, the user data over a period of time, wherein the user data comprises a plurality of total hemoglobin measurements; displaying, by a user interface, a first total hemoglobin measurement of the plurality of total hemoglobin measurements, the displaying comprising: providing, by the user interface, an indication of the first total hemoglobin measurement associated with a first season of a plurality of seasons in a graphical presentation, wherein the graphical presentation comprises a plurality of quadrants, wherein a first quadrant of the plurality of quadrants is associated with the first season and a second quadrant is associated with a second season; displaying, by the user interface, the first total hemoglobin measurement in the first quadrant configured to indicate when the first total hemoglobin measurement was obtained; and providing, by the user interface in the graphical presentation, an optimal indicator, wherein the optimal indicator is configured to indicate an optimal total hemoglobin measurement to allow the user to compare the first total hemoglobin measurement to the optimal total hemoglobin measurement.

In some embodiments, the plurality of total hemoglobin measurements further comprises a second total hemoglobin measurement. In some embodiments, the method further comprises displaying, by the user interface in the graphical presentation, the second total hemoglobin measurement disposed at a location clockwise from the first total hemoglobin measurement. In some embodiments, the method comprises providing, by the user interface, one or more insights configured to notify the user of relevant information about the user data. In some embodiments, the user interface is configured to display a top navigation bar. In some embodiments, the user interface is configured to display a bottom navigation bar.

In some embodiments, the user interface is configured to allow a user to select a filter from a plurality of filters, wherein the filter indicates a physiological parameter from a plurality of physiological parameters. In some embodiments, the user interface is configured to allow a user to select an activity from a plurality of activities, wherein the user interface is configured to display the indication of the first total hemoglobin measurement associated with the activity.

According to some embodiments, a sports training infographic system for presenting user data in a useful way for user use can include a sensor configured to obtain the user data over a period of time, wherein the user data comprises a plurality of total hemoglobin measurements; a database configured to store the user data; and a user interface generated by a system having one or more hardware processors and one or more servers, wherein the user interface is configured to display a first total hemoglobin measurement of the plurality of total hemoglobin measurements, and an indication of the first total hemoglobin measurement associated with a first season of a plurality of seasons in a graphical presentation comprising a plurality of quadrants, wherein a first quadrant of the plurality of quadrants is associated with the first season and a second quadrant is associated with a second season; wherein the user interface is configured to provide the first total hemoglobin measurement in the first quadrant to indicate when the first total hemoglobin measurement was obtained, and wherein the user interface is configured to provide, in the graphical presentation, an optimal indicator configured to indicate an optimal total hemoglobin measurement to allow the user to compare the first total hemoglobin measurement to the optimal total hemoglobin measurement.

According to some embodiments, a sports training infographic method for presenting user data in a useful way for user use can include obtaining, by at least one sensor, the user data over a period of time, wherein the user data comprises a plurality of total hemoglobin measurements; displaying, by a user interface, a first total hemoglobin measurement of the plurality of total hemoglobin measurements, the displaying comprising: providing, by the user interface in a graphical presentation, an indication of the first total hemoglobin measurement according to changes in elevation, wherein the first total hemoglobin measurement is provided according to an elevation at which it was obtained, displaying, by the user interface, an image representing the first total hemoglobin measurement, wherein the user interface is configured to receive a selection by a user of the plurality of total hemoglobin measurements.

In some embodiments, the plurality of total hemoglobin measurements further comprises a second total hemoglobin measurement. In some embodiments, the method further comprises displaying, by the user interface in the graphical presentation, the second total hemoglobin measurement disposed at a location to the right of the first total hemoglobin measurement. In some embodiments, the first total hemoglobin measurement comprises an average of a subset of the plurality of total hemoglobin measurements obtained by the at least one sensor over a predetermined period of time.

In some embodiments, the method comprises calculating, by the sports training infographic, the average of the plurality of total hemoglobin measurements obtained by the at least one sensor over a predetermined period of time. In some embodiments, the predetermined period of time comprises a week. In some embodiments, the user interface is configured to display a top navigation bar. In some embodiments, the user interface is configured to display a bottom navigation bar.

In some embodiments, the user interface is configured to allow a user to select a filter from a plurality of filters, wherein the filter indicates a physiological parameter from a plurality of physiological parameters. In some embodiments, the user interface is configured to allow a user to select an activity from a plurality of activities, wherein the user interface is configured to display the indication of the first total hemoglobin measurement associated with the activity.

According to some embodiments, a sports training infographic system for presenting user data in a useful way for user use can include a sensor configured to obtain the user data over a period of time, wherein the user data comprises a plurality of total hemoglobin measurements; a database configured to store the user data; a user interface generated by a system having one or more hardware processors and one or more servers, wherein the user interface is configured to display a first total hemoglobin measurement of the plurality of total hemoglobin measurements, and provide in a graphical presentation, an indication of the first total hemoglobin measurement according to changes in elevation, wherein the first total hemoglobin measurement is provided according to an elevation at which it was obtained, and wherein the user interface is configured to display an image representing the first total hemoglobin measurement, and wherein the user interface is configured to receive a selection by a user of the plurality of total hemoglobin measurements.

According to some embodiments, a sports training infographic method for presenting user data in a useful way for user use can include obtaining, by at least one sensor, the user data over a period of time, wherein the user data comprises a plurality of physiological parameters; displaying, by a user interface, a total hemoglobin measurement and a resting heart rate of the plurality of physiological parameters, the displaying comprising: providing, by the user interface in a graphical presentation, a comparison of the total hemoglobin measurement and the resting heart rate; displaying, by the user interface, the total hemoglobin measurement in a first side of the graphical presentation; displaying, by the user interface, the resting heart rate in the second side of the graphical presentation; comparing, by the sports training infographic, the total hemoglobin measurement to an optimal total hemoglobin measurement; comparing, by the sports training infographic, the resting heart rate to an optimal resting heart rate; and adjusting, by the user interface, a size of each of the first side and the second side based on the comparison of the total hemoglobin measurement and the comparison of the resting heart rate.

In some embodiments, the method comprises displaying at least one metric calculated based on the user data. In some embodiments, the method comprises displaying an oxygen content measurement around a perimeter of the graphical representation. In some embodiments, the graphical presentation comprises a first flag and a second flag, wherein the first flag extends outwardly from the first side and the second flag extends outwardly from the second side. In some embodiments, the first flag is configured to be selected by a user to send a notification to a second user to congratulate the second user. In some embodiments, the second flag is configured to be selected by a user to send a notification to a second user to encourage the second user.

In some embodiments, the user interface is configured to display a plurality of graphical presentations, wherein each of the plurality of graphical presentations indicates a different user. In some embodiments, the user interface is configured to display a top navigation bar comprising a user profile. In some embodiments, the user interface is configured to display a bottom navigation bar comprising one or more options configured to be selected by the user.

According to some embodiments, a sports training infographic system for presenting user data in a useful way for user use can include a sensor configured to obtain the user data over a period of time, wherein the user data comprises a plurality of physiological parameters; a database configured to store the user data; a user interface generated by a system having one or more hardware processors and one or more servers, wherein the user interface is configured to display a total hemoglobin measurement and a resting heart rate of the plurality of physiological parameters, wherein the user interface is configured to provide in a graphical presentation a comparison of the total hemoglobin measurement and the resting heart rate, wherein the user interface is configured to display the total hemoglobin measurement in a first side of the graphical presentation, wherein the user interface is configured to display the resting heart rate in the second side of the graphical presentation; a comparison module configured to compare the total hemoglobin measurement to an optimal total hemoglobin measurement and configured to compare the resting heart rate to an optimal resting heart rate; and an adjuster configured to adjust a size of each of the first side and the second side based on the comparison of the total hemoglobin measurement and the comparison of the resting heart rate.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIGS. 2A-2B depict an example monitoring device user interface.

FIGS. 3A-3B depict an example monitoring device user interface illustrated in FIG. 1A.

FIGS. 4A-4C depict an example monitoring device user interface illustrated in FIG. 1A.

FIGS. 5A-5B depict an example monitoring device user interface illustrated in FIG. 1A.

FIGS. 6A-6C depict an example monitoring device user interface illustrated in FIG. 1A.

FIGS. 7A-7B depict an example monitoring device user interface.

FIGS. 11A-11C depict an example monitoring device user interface illustrated in FIG. 6A.

FIGS. 12A-12C depict an example monitoring device user interface.

DETAILED DESCRIPTION

I. Introduction

Figure 1A:
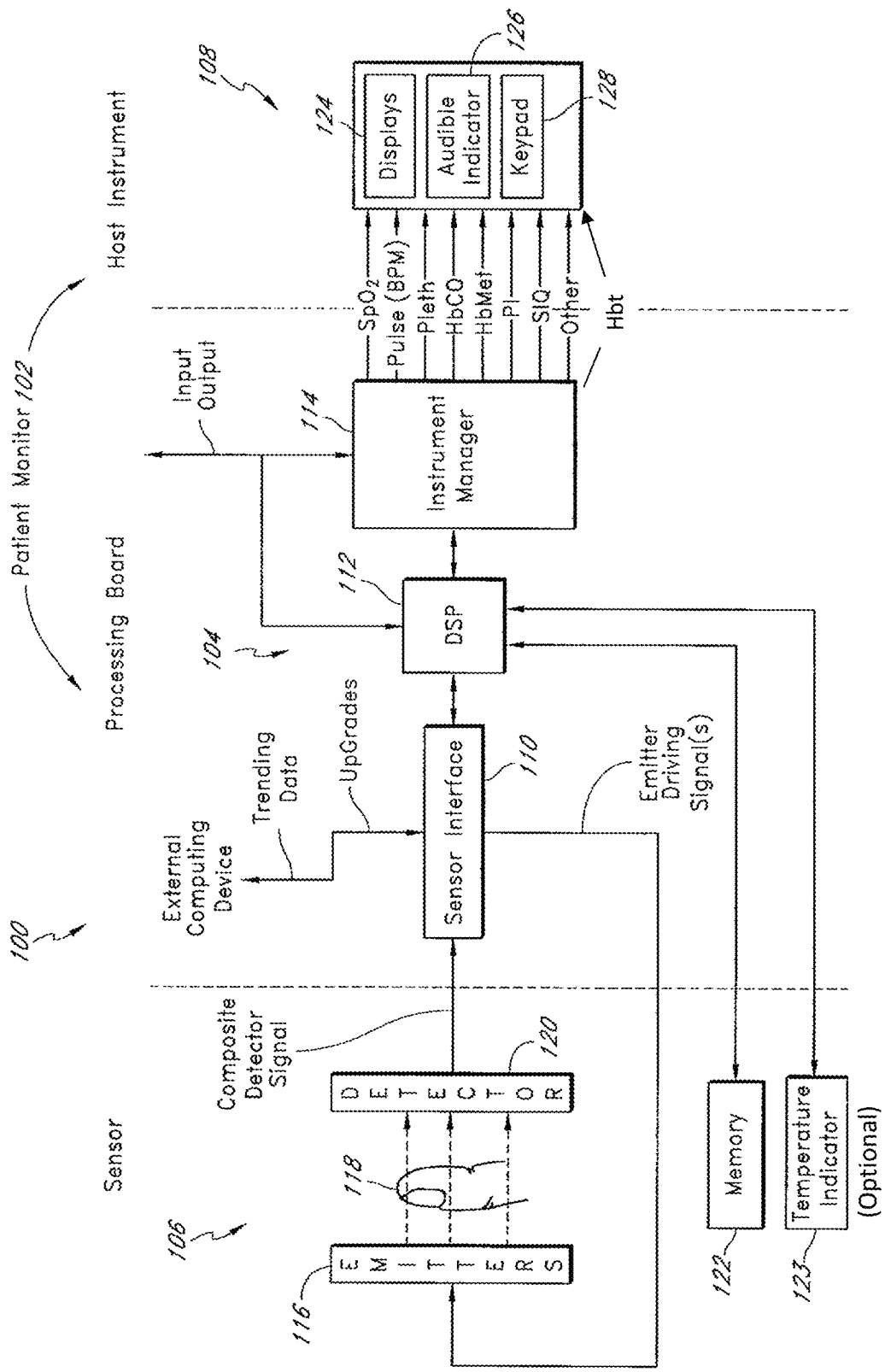
FIG. 1A illustrates a block diagram depicting one embodiment of a computer hardware system configured to run software for implementing one or more embodiments of the sensor system described herein.

Current athletes work extremely hard to produce results and better themselves for competition. They desire to find devices that can track and monitor their physiological parameters to understand themselves and achieve better performance. However many current solutions offer insufficient information (only motion activity trackers, heart rate or some basic pulse oximetry). These current devices can offer insufficient review of meaningful data (just numbers and a basic trend graph). For further insights, athletes may draw their blood once, twice or three times in a year and review the information about certain parameters, such as their Total Hemoglobin Level. Many current systems offer only single peaks into a person's health and in many instances are incapable of giving insightful data review to make better training decisions.

Similarly, many competitive elite athletes go to extreme methods of training, such as living at high elevations or training at high elevations to achieve gains in their Total Hemoglobin levels. Some athletes even sleep in tents to simulate higher elevation at home. This determination and desire leads them to work this way based on published studies that provide general information, rather than an individualized understanding of the time it takes for their specific body to acclimate at different elevations. For example, a team of endurance cyclist could benefit by knowing at what point each of their members acclimates to certain elevations, at what elevation, and by how much. Accordingly, training, style, intensity and location could all be adjusted based on this information. Currently, invasive solutions offer insight into this information and would require an athlete to invasively test multiple times at multiple elevations to learn how they respond to elevation. Invasive procedures would be painful, expensive, and inconvenient (not mobile). Wearable and homecare technology (motion activity trackers, heart rate or some basic pulse oximetry, for example) cannot correctly complete a picture for when and how an athlete responds to elevation. Many wearable and homecare technologies do not provide insightful, intuitive and easy to use visual displays for communicating elevation effects.

In training, one of the struggles people face is to find daily motivation and understand how that determination positively or negatively affects them. Some traditional methods can use social interaction as a form of a support community and motivation to athletes. Many current solutions focus on social aspects solely to keep a user moving. However, many athletes are already active. Many current products help a user focus on a particular route an individual ran and/or the number of steps or elevation they climbed by using an inaccurate activity tracker. Some products allow integration of Heart Rate monitor statistics. However, many individual applications for physiological parameters and social sites fall short of providing valuable insight and comparison of blood parameters or the balance of blood parameters, environment, heart interaction on an individual level or compared to top athletic or Olympic levels.

Certain graphs disclosed herein, such as the trend graph and Yin-Yang display can offer the ability to filter the parameter and activity being displayed. This allows a user to choose to show resting measurements for particular days and only post some or all workout measurements. Thus, the user can filter certain results. The ability to filter can be advantageous because a user's hemoglobin value can vary drastically during a day, for example. In order for users to be able to see small seasonal variations, users can filter collected data to see the most stable and repeatable time of the day to measure, which could be first of day resting period. Similarly, the user can use the devices disclosed herein to determine the most stable and repeatable time of day to measure and view a resting pulse rate.

Advantageously, some embodiments of the system disclosed herein can allow the system to filter activity displayed in the graphs. In many instances, the system can be configured to allow a user to choose to display hemoglobin (tHb) or Pulse Rates (PR). Other parameters, including Functional and Fractional Oxygen Saturation, Oxygen Content, Carbon Monoxide, Methemoglobin, Perfusion Index, Pleth Variability Index, and/or Respiration Rate, among others, can be displayed through the system.

Alternative embodiments can include other visual focus and identification elements. In some embodiments, color and glowing effects can be used to indicate points at which the user's data reflects a significant change. In some embodiments, a user may see a 3*d* sphere that swells in size to reflect the climb in tHb values. In yet other embodiments of the system disclosed herein, additional lifestyle integration variations of sensors (such as bands, watches, shirts etc.) as well as variations on visual display to 3D augmented reality or heads up display units can be used. In some embodiments, the one or more graphs can add a multiple factor overlay. In this embodiment, the system can compare seasonal variation of atmospheric pollution levels with seasonal variations in the athlete's noninvasive CO readings or the seasonal variations in temperature with pulse rate. In additional embodiments, the system can compare elevation and tHb with the changes of atmospheric pollution levels as well as cross reference with multiple parameters. In additional embodiments, the system can compare Respiration Rate (Pleth acquired or acoustic or ecg acquired) compared with Heart rate and Pollen levels would let an athlete with respiratory conditions, such as asthma. Advantageously, embodiments of the system disclosed herein can allow a user to understand a balance of their respiratory system.

This disclosure describes embodiments of noninvasive sensor systems that can enable a user to view, compare, and/or information relating to the respiratory system, for example, via a computing device, which may contain more advanced functionality than traditional systems and devices. The computing device can be, for instance, a cellphone or smartphone, tablet, laptop, personal digital assistant (PDA), and/or the like.

User Interfaces

Generally, the embodiments described herein can depict several example user interfaces that may be implemented in a user computing device. The user interfaces shown can depict example displays generated by the noninvasive sensor system and may be implemented in any of the user devices described herein. The example user device shown in FIGS. 2A-12C may have any of the features of the user devices described herein.

The user interfaces shown may be implemented in a mobile application such as an application that runs on a mobile operating system such as the Android™ operating system available from Google™ or the iOS™ operating system available from Apple™. Alternatively, or in addition to being a mobile application, the user interfaces shown can be implemented in a web application that runs in a browser.

The user interfaces shown are merely examples that illustrate some example embodiments described herein and may be varied in other embodiments. For instance, user interface controls shown may include buttons, touch-selective components and the like which may be altered to include any type of user interface control including, but not limited to, checkboxes, radio buttons, select boxes, drop-down boxes, textboxes or any combination of the same. Likewise, the different user interface controls may be combined or their functionality may be spread apart amongst additional controls while retaining the similar or same functionality as shown and described herein with respect to FIGS. 2A through 12C. Although touchscreen interfaces are shown, other devices may implement similar user interfaces with other types of user input devices such as a mouse, keyboard, stylus, or the like.

FIG. 1A illustrates a block diagram of an exemplary embodiment of a user monitoring system 100. As shown in FIG. 1A, the system 100 includes a user monitor 102 comprising a processing board 104 and a host instrument 108. The processing board 104 communicates with a sensor 106 to receive one or more intensity signal(s) indicative of one or more parameters of tissue of a user. The processing board 104 also communicates with a host instrument 108 to display determined values calculated using the one or more intensity signals. According to an embodiment, the processing board 104 comprises processing circuitry arranged on one or more printed circuit boards capable of installation into the monitor 102, or capable of being distributed as some or all of one or more OEM components for a wide variety of host instruments monitoring a wide variety of user information. In an embodiment, the processing board 104 comprises a sensor interface 110, a digital signal processor and signal extractor ("DSP" or "processor") 112, and an instrument manager 114. In general, the sensor interface 110 converts digital control signals into analog drive signals capable of driving sensor emitters, and converts composite analog intensity signal(s) from light sensitive detectors into digital data.

In an embodiment, the sensor interface 110 manages communication with external computing devices. For example, in an embodiment, a multipurpose sensor port (or input/output port) is capable of connecting to the sensor 106 or alternatively connecting to a computing device, such as a personal computer, a PDA, additional monitoring equipment or networks, or the like. When connected to the computing device, the processing board 104 may upload various stored data for, for example, off-line analysis and diagnosis. The stored data may comprise trend data for any one or more of the measured parameter data, plethysmograph waveform data acoustic sound waveform, or the like. Moreover, the processing board 104 may advantageously download from the computing device various upgrades or executable programs, may perform diagnosis on the hardware or software of the monitor 102. In addition, the processing board 104 may advantageously be used to view and examine user data, including raw data, at or away from a monitoring site, through data uploads/downloads, or network connections, combinations, or the like, such as for customer support purposes including software maintenance, customer technical support, and the like. Upgradable sensor ports are disclosed in copending U.S. application Ser. No. 10/898, 680, filed on Jul. 23, 2004, titled "Multipurpose Sensor Port," incorporated by reference herein.

As shown in FIG. 1A, the digital data is output to the DSP 112. According to an embodiment, the DSP 112 comprises a processing device based on the Super Harvard ARChitecture ("SHARC"), such as those commercially available from Analog Devices. However, a skilled artisan will recognize from the disclosure herein that the DSP 112 can comprise a wide variety of data and/or signal processors capable of executing programs for determining physiological parameters from input data. In particular, the DSP 112 includes program instructions capable of receiving multiple channels of data related to one or more intensity signals representative of the absorption (from transmissive or reflective sensor systems) of a plurality of wavelengths of emitted light by body tissue. In an embodiment, the DSP 112 accepts data related to the absorption of eight (8) wavelengths of light, although an artisan will recognize from the disclosure herein that the data can be related to the absorption of two (2) to sixteen (16) or more wavelengths.

FIG. 1A also shows the processing board 104 including the instrument manager 114. According to an embodiment, the instrument manager 114 may comprise one or more microcontrollers controlling system management, including, for example, communications of calculated parameter data and the like to the host instrument 108. The instrument manager 114 may also act as a watchdog circuit by, for example, monitoring the activity of the DSP 112 and resetting it when appropriate.

The sensor 106 may comprise a reusable clip-type sensor, a disposable adhesive-type sensor, a combination sensor having reusable and disposable components, or the like. Moreover, an artisan will recognize from the disclosure herein that the sensor 106 can also comprise mechanical structures, adhesive or other tape structures, Velcro wraps or combination structures specialized for the type of user, type of monitoring, type of monitor, or the like. In an embodiment, the sensor 106 provides data to the board 104 and vice versa through, for example, a user cable. An artisan will also recognize from the disclosure herein that such communication can be wireless, over public or private networks or computing systems or devices, or the like.

As shown in FIG. 1A, the sensor 106 includes a plurality of emitters 116 irradiating the body tissue 118 with differing wavelengths of light, and one or more detectors 120 capable of detecting the light after attenuation by the tissue 118. In an embodiment, the emitters 116 comprise a matrix of eight (8) emission devices mounted on a flexible substrate, the emission devices being capable of emitting eight (8) differing wavelengths of light. In other embodiments, the emitters 116 may comprise twelve (12) or sixteen (16) emitters, although other numbers of emitters are contemplated, including two (2) or more emitters. As shown in FIG. 1A, the sensor 106 may include other electrical components such as, for example, a memory device 122 comprising an EPROM, EEPROM, ROM, RAM, microcontroller, combinations of the same, or the like. In an embodiment, other sensor components may include a an optional temperature determination device 123 or other mechanisms for, for example, determining real-time emission wavelengths of the emitters 116.

The memory 122 may advantageous store some or all of a wide variety data and information, including, for example, information on the type or operation of the sensor 106; type or identification of sensor buyer or distributor or groups of buyer or distributors, sensor manufacturer information, sensor characteristics including the number of emitting devices, the number of emission wavelengths, data relating to emission centroids, data relating to a change in emission characteristics based on varying temperature, history of the sensor temperature, current, or voltage, emitter specifications, emitter drive requirements, demodulation data, calculation mode data, the parameters for which the sensor is capable of supplying sufficient measurement data (e.g., HpCO, HpMet, HbT, or the like), calibration or parameter coefficient data, software such as scripts, executable code, or the like, sensor electronic elements, whether the sensor is a disposable, reusable, multi-site, partially reusable, partially disposable sensor, whether it is an adhesive or non-adhesive sensor, whether the sensor is a reflectance, transmittance, or transreflectance sensor, whether the sensor is a finger, hand, foot, forehead, or ear sensor, whether the sensor is a stereo sensor or a two-headed sensor, sensor life data indicating whether some or all sensor components have expired and should be replaced, encryption information, keys, indexes to keys or hash functions, or the like, monitor or algorithm upgrade instructions or data, some or all of parameter equations, information about the user, age, sex, medications, and other information that may be useful for the accuracy or alarm settings and sensitivities, trend history, alarm history, or the like. In an embodiment, the monitor may advantageously store data on the memory device, including, for example, measured trending data for any number of parameters for any number of users, or the like, sensor use or expiration calculations, sensor history, or the like.

FIG. 1A also shows the user monitor 102 including the host instrument 108. In an embodiment, the host instrument 108 communicates with the board 104 to receive signals indicative of the physiological parameter information calculated by the DSP 112. The host instrument 108 preferably includes one or more display devices 124 capable of displaying indicia representative of the calculated physiological parameters of the tissue 118 at the measurement site. In an embodiment, the host instrument 108 may advantageously comprise a handheld housing capable of displaying one or more of a pulse rate, plethysmograph data, perfusion quality such as a perfusion quality index ("PI™"), signal or measurement quality ("SQ"), values of blood constituents in body tissue, including for example, $SpO_2$, HbCO, HbMet, Hbt, or the like. In other embodiments, the host instrument 108 is capable of displaying values for one or more of Hbt, Hb, blood glucose, bilirubin, or the like. The host instrument 108 may be capable of storing or displaying historical or trending data related to one or more of the measured values, combinations of the measured values, plethysmograph data, or the like. The host instrument 108 also includes an audio indicator 126 and user input device 128, such as, for example, a keypad, touch screen, pointing device, voice recognition device, or the like.

In still additional embodiments, the host instrument 108 includes audio or visual alarms that alert caregivers that one or more physiological parameters are falling below predetermined safe thresholds. The host instrument 108 may include indications of the confidence a caregiver should have in the displayed data. In a further embodiment, the host instrument 108 may advantageously include circuitry capable of determining the expiration or overuse of components of the sensor 106, including, for example, reusable elements, disposable elements, or combinations of the same.

Although described in terms of certain embodiments, other embodiments or combination of embodiments will be apparent to those of ordinary skill in the art from the disclosure herein. For example, the monitor 102 may comprise one or more monitoring systems monitoring parameters, such as, for example, vital signs, blood pressure, ECG or EKG, respiration, glucose, bilirubin, or the like. Such systems may combine other information with intensity-derived information to influence diagnosis or device operation. Moreover, the monitor 102 may advantageously include an audio system, preferably comprising a high quality audio processor and high quality speakers to provide for voiced alarms, messaging, or the like. In an embodiment, the monitor 102 may advantageously include an audio out jack, conventional audio jacks, headphone jacks, or the like, such that any of the display information disclosed herein may be audiblized for a listener. For example, the monitor 102 may include an audible transducer input (such as a microphone, piezoelectric sensor, or the like) for collecting one or more of heart sounds, lung sounds, trachea sounds, or other body sounds and such sounds may be reproduced through the audio system and output from the monitor 102. Also, wired or wireless communications (such as Bluetooth or WiFi, including IEEE 801.11a, b, or g), mobile communications, combinations of the same, or the like, may be used to transmit the audio output to other audio transducers separate from the monitor 102.

For example, patterns or changes in the continuous noninvasive monitoring of intensity-derived information may cause the activation of other vital sign measurement devices, such as, for example, blood pressure cuffs.

II. Visual Multi Quadrant Infographic Display

Traditional methods of monitoring and displaying certain physiological parameters can lack the ability to monitor certain physiological parameters noninvasively. Traditional methods can take a long period of time to display collected data, including the physiological parameters. Rather, the systems disclosed herein can measure and display the physiological parameters within minutes. For example, embodiments of the system disclosed herein can frequently measure physiological parameters multiple times a day to build a substantial data set. The system can measure physiological parameters 1 to 2, 2 to 3, 3 to 4, 4 to 5, 5 to 6, and/or 1 to 6 or more times a day. In some embodiments, the physiological parameters can be displayed in an informative visual graphic display, such as a trend graph 230. The trend graph can be user-friendly and provide a well-designed display. For example, the trend graph can include a multi quadrant seasonal variation spider graph, as illustrated in FIGS. 2A-6C.

The trend graph 230 can provide a detailed look at all data points of the physiological parameters 203 within one or more seasonal years. In some embodiments, the trend graph 230 can display the physiological parameters 203 collected within one, two, three, four, five, six, seven, eight, nine, or ten or more years. Advantageously, the trend graph can allow the user to quickly and easily identify whether a seasonal variation exists in their physiological parameters.

Generally, users can have seasonal variation in several physiological parameters, such as tHb. As discussed above, the system 100 can collect user data 202 including information about a user at various intervals. The user data 202 can include a plurality of data points. For example, the system can measure and collect the data points at regular intervals throughout a period of time, such as an hour, day, month, and/or year. Advantageously, the system 100 can allow the user to track and assess user data 202 over time. For example, the system 100 can provide various points of comparison to the user through the user interface 200 so the user can make judgments based on all or a portion of the user data 202, rather than at a particular point in time. In some embodiments, it can be advantageous to measure, collect, and/or calculate the user data 202 at consistent intervals. In such configurations the system 100 can analyze more user data 202 to interpret a complete set of user data so that the system may interpret the user data 202 more accurately. In some configurations, the system 100 can provide user data 202 that can allow the user to make more accurate judgments about their physiological parameters. Accordingly, the user can have the ability to increase their performance based on more accurate results and adjust their diet and exercise routines. In some embodiments however, the system can measure and collect the user data at irregular intervals.

The user data 202 can include one or more data points corresponding to one or more physiological parameters 203. For each physiologic parameter 203, the system can assign certain information relating to each recorded physiologic parameter. For example, the system can assign a time, date, season, and/or location to each recorded physiologic parameter. Generally, the system can display information relating to the user data 202, such as whether seasonal variation occurs in a user's tHb and/or PR, when the variation occurs, and/or how the variation affects the user. In some embodiments, the user would be able to view the display information within seconds. Accordingly, the display information can help a user determine how to adjust a training routine and/or diet, for example, to achieve better performance results throughout the year.

The user can select from a plurality of filters and a plurality of physiological parameters. When the user selects a filter and a type of physiological parameter, the system 100 can display a user interface 200. The user interface 200 can be presented in an aesthetically pleasing and/or user friendly manner. The user interface 200 can display the user data 202, insights 206 and/or the one or more graphs 204 that allows the user to quickly view information. To view particular information, the user can select a filter from a plurality of filters. The plurality of filters can include filters that can dictate how the user data 202 is displayed, such as by season and elevation. In some embodiments, the user can select one or more physiological parameters 203. In some embodiments, the user can select an activity from the plurality of activities, such as pre-workout, pre-hydration, during workout, post-workout and/or post-hydration, among others. The user can select all activities from the plurality of activities. The system 200 can display the user interface 200 within approximately 500 milliseconds to 1 second after a filter is selected.

For example, a user can select a seasonal filter from the plurality of filters, a physiological parameter 203, and an activity from the plurality of activities. Upon the user's selection, the system 100 can display a user interface 200. FIGS. 2A and 2B illustrate an example of the user interface 200 in which the user has selected the seasonal filter. The user interface 200 can include a top navigation bar 208, one or more graphs 204, one or more insights 206, and a bottom navigation bar 212. The one or more graphs can include the user data 202 and the one or more physiological parameters 203.

The one or more graphs 204 can include the trend graph 230. The trend graph 230 can include a horizontal axis and a vertical axis. For example, the horizontal axis and the vertical axis can indicate the value of the physiological parameter 203 selected by the user.

The trend graph 230 can include a plurality of quadrants 234 to display the display information. In some embodiments, the trend graph 230 can include one, two, three, four, five, six, seven, eight, nine, or ten or more quadrants 234. For example, the graph 230 can include a first quadrant 234A, a second quadrant 234B, a third quadrant 234C, and a fourth quadrant 234D.

Each of the plurality of quadrants 234 can display information that corresponds to a particular seasonal time. The number of quadrants displayed in the trend graph 230 can depend on several factors, including a geographic location. For example, in geographic locations having four seasons, the trend graph 230 can include four quadrants associated with each of the four seasons. In the illustrated embodiment, the first quadrant 234A can correspond to Winter. The second quadrant 234B can correspond to Spring. The third quadrant 234C can correspond to Summer. The fourth quadrant 234D can correspond to Fall. In some embodiments, each quadrant of the plurality of quadrants 234 can be displayed in the same color. In some embodiments, each quadrant of the plurality of quadrants 234 can be displayed using different colors.

The user data 202 can be displayed in the trend graph 230 along a plurality of data rings 238. Each data point of the user data 202 can be displayed clockwise around a center of the data rings 238. In some embodiments, each data point of the user data 202 can be displayed counterclockwise around a center of the data rings 238. The data points can be presented in degree increments along the data rings 238. Each data point can represent a measurement taken and/or calculated by the system 100. For example, the system can record measurements of the user data 202 once a day. In this example, after 360 days, the trend graph 230 could display the user data 202 along a full ring of the data rings 238.

FIG. 3A illustrates an embodiment of a zoom user interface 250, which can display a close-up view of the trend graph 230. As shown in the FIG. 3A, the trend graph 230 can include a plurality of indicator rings 242 to illustrate various ranges and/or values corresponding to each particular physiological parameter 203 selected by the user. The plurality of indicator rings 242 can present an optimal range of physiological parameters 203. For example, the trend graph 230 can include a first indicator ring 242A of the plurality of indicator rings 242. The first indicator ring 242A can represent an optimal value for the particular physiological parameter 203 selected by the user. The optimal value and/or range can be based on one or more user inputs, such as the user's age and/or gender. The first indicator ring 242A can be disposed towards the center of the trend graph 230. The first indicator ring 242A can be disposed towards the outer periphery of the trend graph 230. The first indicator ring 242A can be disposed towards the inner ring of the trend graph 230.

In some embodiments, the trend graph 230 can include a second indicator ring 242B and a third indicator ring 242C. The second indicator ring 242B can indicate a lower value and/or range of the optimal range. The second indicator ring 242B can be disposed towards an inner ring of the trend graph 230 interior of the first indicator ring 242A, for example. In some embodiments, the trend graph 230 can include a third indicator ring 242C. The third indicator ring 242C can indicate an upper value and/or range of optimal range. The third indicator ring 242C can be disposed towards an outer ring of the trend graph 230 outwards from the first indicator ring 242A, for example.

Generally, the close-up view of the trend graph 230 can be presented to the user when the user activates one or more zoom user interfaces 250. Activating the zoom user interface 250 can allow a user to observe individual data points of the user data 202, among other detailed information displayed in the trend graph 230. The zoom user interface can allow the user to understand the user data 202 and gain a better understanding of how to adjust their diet and/or exercise routine, which can enhance the user's performance. The zoom user interface 250 can display information such as the time, date, season, and/or location assigned to each monitored, measured, and/or calculated data point.

When the zoom user interface 250 is activated, the zoom user interface can pop up from the user interface 200, overlap at least a portion of the user interface 200, and/or replace the user interface 200. To activate the zoom user interface 250, the user can apply a plurality of zooming gestures. The zooming gestures can include a double tap, a finger zoom, and/or a pan, among other gestures. For example, the user can double tap on the user interface 200 to activate the zoom interface 250. The user can double tap any area of the user interface 200, including any portion of the trend graph 230. The zoom interface 250 can display the portion in which the user double tapped in the user interface 200 to view the trend graph 230 in more detail. In some embodiments, when the system 100 displays the zoom user interface 250, the user can double tap the zoom user interface 250 to activate the user interface 200 and view the entire trend graph 230.

In some examples, the user can activate the zoom interface 250 by applying finger zoom gesture. For example, the user can touch the user interface 200 with at least two fingers and slide the at least two fingers apart from one another. This configuration can allow the user to gradually zoom in on a particular portion of the user interface 200 with a gradient zoom. The zoom interface 250 can be displayed gradually and can depend on the speed and/or extent of the finger zoom (for example, how far and/or how fast the user slides their fingers apart on the user interface 200). In some embodiments, the zoom interface 250 can display up to one month of data points. In some embodiments, the zoom interface 250 can display up to an hour, a day, and/or a year of data points. In some embodiments, the user can zoom out from the zoom interface 250 and activate the user interface 200 by pinching at least two fingers together. The seasonal variation interface 250 can be displayed gradually and can depend on the speed and/or extent of the finger zoom (for example, how far and/or how fast the user slides their fingers together on the zoom user interface 200).

In some embodiments, the user can navigate to various portions of the zoom interface 250. For example, the user can pan in any direction by swiping along the zoom interface 250. If the user pans too far to the edge of the zoom interface 250, for example, the zoom interface can indicate to the user that the user has reached the edge of the zoom interface 250. For example, at the edge of the zoom interface 250, the zoom interface can bounce back and/or rubber band.

FIGS. 6A-6C illustrate examples of the seasonal variation user interface that includes a varying number of data points of the user data 202. As shown in FIGS. 6A-6C, the user interface 200 can display one or more insights 206. The insights 206 can present to the user a general summary of the user data 202. For example, if no data has been recorded, the insights 206 can notify the user that no data is available (see FIG. 6A). In embodiments that include insufficient data, for example, when only one data point of the user data 202 has been measured, calculated, and/or recorded by the system 100, the insights 206 can notify the user that more user data is required (see FIG. 6B). In some embodiments, the insights 206 can remind the user to use the system 100 to monitor and/or measure user data. The insights can remind the user to use the system 100 to measure user data 206 more regularly, more often, and/or at different times.

In some embodiments, the system 100 can determine that a sufficient amount of user data 202 has been measured, calculated, and/or recorded. In some embodiments, the user interface 200 can display the user data within the trend graph 230 when a sufficient amount of user data 202, for example, at least two data points, has been measured, calculated, and/or recorded by the system 100. In some embodiments, the user interface 200 can display the user data within the trend graph 230 even when an insufficient amount of user data has been measured, calculated, and/or recorded by the system 100.

FIG. 6A illustrates an embodiment of the system 100 wherein no data is available. In this configuration, the user interface 200 can notify the user that no data is available to be displayed. For example, the insights 206 can present to the user that no data is available. In some embodiments, the trend graph 230 can present to the user that no data is available. For example, the trend graph 230 can display no data points of the user data 202. In such a configuration, the trend graph 230 can display text, an image, and/or another indication that no data is available. In this configuration, the trend graph 230 can display a range of years. The trend graph 230 can display a range of measurements on the horizontal and/or vertical axis.

In some embodiments in which no data has been measured, calculated, and/or recorded, the system 100 may not allow for a user to activate the zoom interface 250. In some embodiments, the system 100 may not allow for a user to apply at least some of the zooming gestures 254. In some embodiments, the seasonal variation user interface 230 does not display the user data 202 because of certain selections and/or filters selected by the user. For example, the user can select a specific activity, time period, physiological parameter, and/or filter for which no data has been monitored, measured, and/or calculated. In such configurations, the user interface 200 can notify and/or otherwise present to the user that no data is available within the particular filter selected.

FIG. 6B illustrates an embodiment of the user interface 200 wherein one data point 246 has been monitored, measured, and/or calculated by the system 100. In some embodiments, the one data point can be an insufficient amount of user data 202. In such configurations, the insight 206 can indicate to the user that an insufficient amount of data has been monitored, measured, and/or calculated by the system 100. In this embodiment, the data point is displayed on the trend graph 230. The data point can be displayed in the form of a line and/or a point. As shown in the trend graph 230, the data point can be displayed as a line that begins at the center of the graph, where the horizontal axis and the vertical axis intersect, for example, and extends outwardly to the ring indicating the value of the physiological parameter measured.

Some embodiments of the user interface 200 can display more than one data point. For example, FIG. 6C illustrates an embodiment of the user interface 200 including at least two data points 246. In some embodiments, at least two data points can be a sufficient amount of user data 202. In such configurations, consecutive data points 246 can be connected by one or more connecting lines 248. For example, the connecting lines 248 can be displayed connecting consecutive data points 246 at the point of the value of the physiological parameter 203. The connecting lines 248 can be straight or rounded. In some embodiments, the connecting lines 248 can be circular. In some embodiments, the connecting lines 248 can form a web-like structure. The area beneath the connecting lines 248 can be shaded towards a point at the intersection between the horizontal axis and the vertical axis disposed at the center of the trend graph 230.

In some embodiments, the connecting lines 248 can connect data points 246 recorded one, two, three, four, five, six, seven, eight, nine, and/or ten or more days apart. In some embodiments, the connecting lines 248 can connect data points 246 recorded 11, 12, 13, 14, 15, 16, 17, 18, 19, and/or 20 or more days apart. In some embodiments, the connecting lines 248 can connect data points 246 recorded one, two, three, four, five, six, seven, eight, nine, and/or ten or more weeks apart. Some embodiments a rounded connecting line 248 can connect two data points. In some embodiments, the system 100 can average two or more data points. In such configurations, user interface 200 can display connecting line 248 at the average of the two or more data points. In certain embodiments, the increment of the data points displayed by the user interface 200 in the trend graph 230 can indicate which data points are connected by the connecting line 248.

FIGS. 2A and 2B illustrate the top navigation bar 208 of the user interface 200. The top navigation bar 208 can be animated by the user interface 200. For example top navigation bar 208 can flip, spin, fade, and/or otherwise displayed with an animation. Top navigation bar 208 can include a title portion 220, a subtitle portion 224, stretch icon 216, a filter stack icon 218.

The title portion 220 can describe the type graph 204 that is displayed by the user interface 200. For example, the user interface 200 can display the trend graph 230. As illustrated in FIG. 2A, title portion 220 describes the type of graph 204.

The subtitle portion 224 can describe the type of filter selected and applied to user interface 200. For example, the user can select one or more filters from the plurality of filters, one or more physiological parameters, and one or more activities from the plurality of activities. By selecting the one or more filters, one or more physiological parameters, and/or the one or more activities, the user can access, by the system, a list of the plurality of filters, plurality of physiological parameters, and/or plurality of activities by selecting and activating the filter stack icon 218.

When the user selects the filter stack icon 218, the user interface 200 can display a filter user interface 260. FIGS. 5A and 5B illustrates an example of the filter user interface 260. The filter user interface 260 can provide a list of the plurality of filters, the plurality of activities, and/or the plurality of physiological parameters. The user can select one or more of the plurality of filters, the plurality of activities, and/or the plurality of physiological parameters. After selecting one or more of the plurality of filters, the plurality of activities, and/or the plurality of physiological parameters, the user can submit the selections by selecting a submit option. The system can receive the submission. The system 100 can update the data points depending on the user's selection and display a new version of the trend graph 230 in the user interface 200. In some embodiments, the system 100 dynamically updates the trend graph 230 according to the user's selections in real time.

In some embodiments, selection of the stretch icon 216 of the top navigation bar 208 can allow the title portion 220 to be displayed in the user interface 200 in full screen. In some embodiments, selection of the stretch icon 216 of the top navigation bar 208 can allow the title portion 220 to be displayed in the user interface 200 in the original configuration of the top navigation bar 208.

FIGS. 2A and 2B illustrate the bottom navigation bar 212 of the user interface 200. The bottom navigation bar 212 can be animated by the user interface 200. For example the bottom navigation bar 212 can flip, spin, fade, and/or otherwise be displayed with an animation. The bottom navigation bar 212 can include an information icon 226 and a share icon 228. In some embodiments, the system 100 can flip the bottom navigation bar 212 to reveal additional icons. Additional user interfaces can be accessed through selection by the user of the information icon 226 and/or the share icon 228, for example.

In some embodiments, the user can select the information icon 226 to access an information user interface 270. FIG. 3B illustrates an example of the information user interface 270. When the information user interface 270 is activated, the information user interface 270 can pop up from the user interface 200, overlap at least a portion of the user interface 200, and/or replace the user interface 200.

The information user interface 270 can include an explanation of the trend graph 230. The information user interface 270 can include instructions for interpreting trend graph 230. In some embodiments, the information user interface 270 can include a summary 272 of the display information including the trend graph 230. The summary can be scrollable in some examples.

In some embodiments, the information user interface 270 can include a list 274 of the plurality of physiological parameters 203. The information user interface 270 can display and/or highlight the one or more physiological parameters selected by the user. Each of the physiological parameters can be represented by an image and/or icon 275. In some embodiments, the information user interface 270 can include a list 276 of the plurality of activities. The information user interface 270 can display the one or more activities selected by the user. Each of the activities can be represented by an image and/or icon 277. In some embodiments, the information user interface 270 can allow the user to select the size adjustment icon 278. Selection of the size adjustment icon 278 can cause the size of the text to increase or decrease. In some embodiments, selection of the size adjustment icon 278 can cause the size of the images to increase or decrease.

The system 100 can include sharing capabilities. In some embodiments, the user can select the share icon 228 to access a sharing user interface 280 that can include a sharing menu with several options for sharing certain information to third parties. FIGS. 4A-4C illustrate an example of the sharing user interface 280. When the sharing user interface 280 is activated, the sharing user interface 280 can pop up from the user interface 200, overlap at least a portion of the user interface 200, and/or replace the user interface 200.

The sharing user interface 280 can allow the user to share information and/or a shared image 282 to third parties. The sharing menu can display a plurality of icons 285 representing third-party applications and/or websites for sharing the shared image 282 and/or other information. The plurality of icons can be displayed in rows, for example. The rows of icons can be scrollable in the left, right, up, and/or down direction to display additional icons. The user can select one or more of the plurality of icons to share certain user data and/or a shared image 282, as described below. For example, the shared image 282 and/or other information can be shared via digital or physical methods. In some embodiments, the shared image 282 and/or other information can be delivered to third parties through SMS, email, printing, and/or social media, among other sharing platforms. The sharing capabilities of the system 100 can allow the user to share the user data 202 with third parties, including a trainer, for example, who are invested in the user's athletic performance and success.

In some embodiments, the user data 202 can be shared as part of the trend graph 230. The sharing user interface 280 can allow the user to share a screenshot of all or a portion of the season variation user interface 200. In some embodiments, the sharing user interface 280 can allow the system to share an image 282 (see FIG. 4C) that includes all or a portion of the season variation user interface 200 and additional information. For example, the shared image 282 can include a view similar to the view displayed by the zoom user interface 250. In some embodiments, the shared image 282 can include a watermark 284 and a summary title 286. The watermark 284 can indicate a brand, for example. In some embodiments, the summarizing title 286 can display a summary of the filter and/or physiological parameter 203 selected by the user, for example. The shared image 282 can allow third parties to quickly view and interpret the user data 202 provided by the system 100. In some embodiments, the user can select certain data to be shared to the third parties. In some embodiments, the user data 202 can be shared in the form of raw data.

If a user decides to cancel a request to share the user data and/or shared image, the user can cancel the request. For example, the user can select a cancel icon 288 displayed by the sharing user interface 280. In some embodiments, the user can simply select an area outside of the sharing menu displayed by the sharing user interface 280.

III. Visual Elevation Infographic Display

FIGS. 7A-11C illustrate an embodiment of the user interface 300. The user interface 300 is similar or identical to the user interface 200 discussed above in many respects. Accordingly, numerals used to identify features of the user interface 300 are incremented by a factor of one hundred to identify certain similar features of the user interface 300. For example, as shown in FIGS. 7A and 7B, the user interface 300 can include a top navigation bar 308, one or more graphs 304, and a bottom navigation bar 312 as described above in connection with the user interface 200. The top navigation bar 308 can include a title portion 320, a subtitle portion 324, a stretch icon 316 and/or a filter stack icon 308. The bottom navigation bar 312 can include an information icon 326 that can be selected to display an information user interface 370 (see FIG. 8B) and a share icon 328 that can be selected to display a share user interface 380 that can include a sharing menu (see FIGS. 9A-9C) for providing sharing capabilities.

Figure 10B:
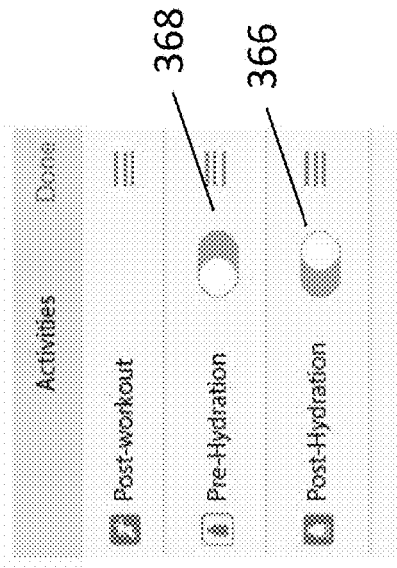
FIGS. 10A-10C depict an example monitoring device user interface illustrated in FIG. 6A.
Figure 10C:
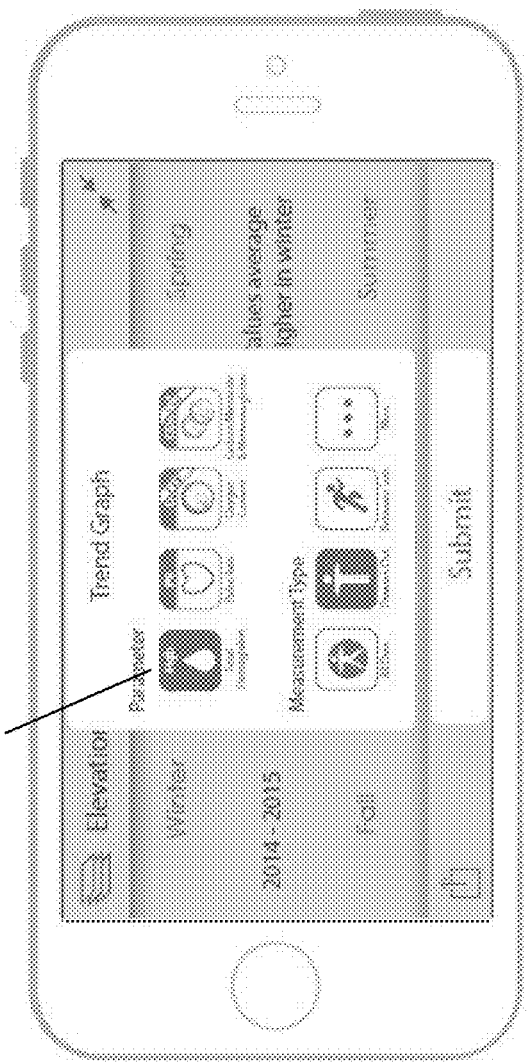
Figure 10A:
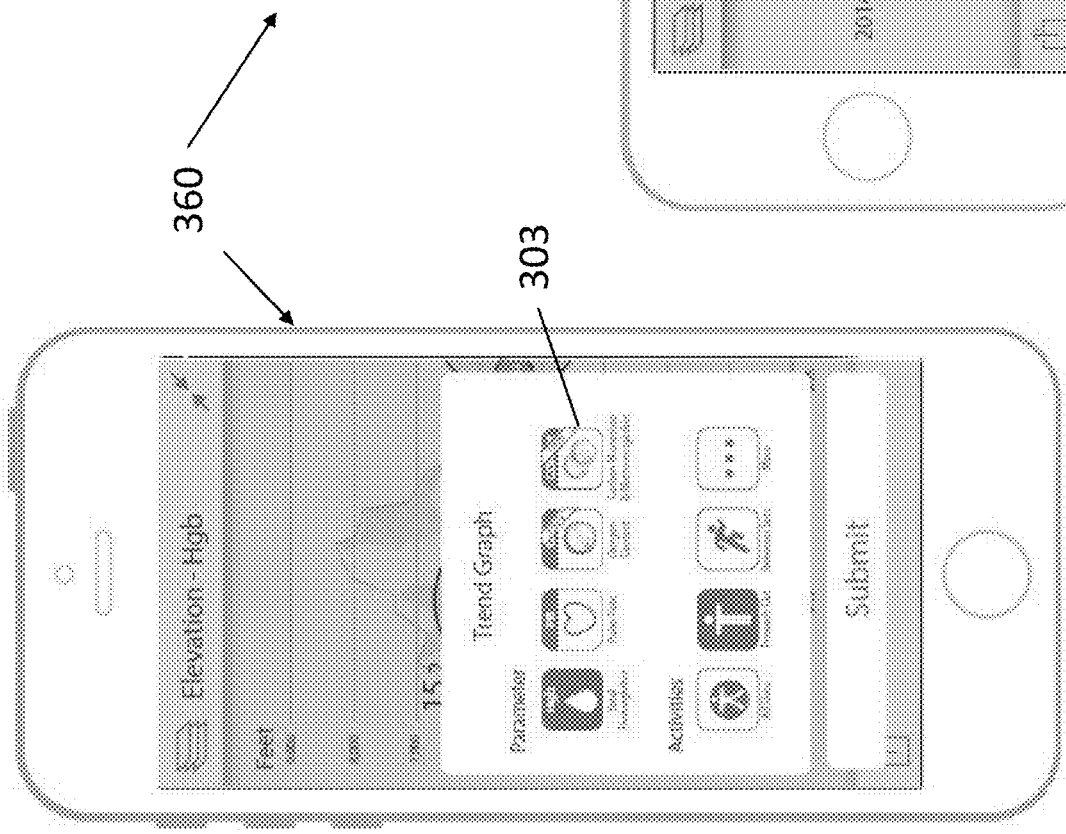

User data 302 can include one or more data points corresponding to one or more physiological parameters 303 as described above in connection with the user interface 200. The user interface 300 can include any one, or any combination, of the features of the user interface 200. For example, the user interface 300 can be substantially similar to the user interface 200. However, in some embodiments, the user interface 300 can illustrate an example of the user interface 200 in which the user has selected an elevation filter (see FIGS. 7A and 7B). To select a filter, the user can select the filter stack icon 318. When the system receives the request from the user, the system can cause the user interface 300 to display a filter user interface 360. FIGS. 10A-10C illustrate an example of the filter user interface 360. The filter user interface 360 can include a list of the plurality of physiological parameters 330 and/or the plurality of activities. FIG. 10B provides an example of the filter user interface 360 illustrating that the user has selected activity 366, but did not select activity 368.

In some embodiments, the user data 302 can be displayed in one or more graphs 304, such as a trend graph 330. In the illustrated embodiment, the trend graph can include an elevation graph. The trend graph 330 can provide a detailed look at all or a selection of the physiological parameters monitored, measured and/or calculated by the system.

The trend graph 330 can allow the user to view the user data over time. The trend graph 330 can allow the user to view the user data 302, such as the selected physiological parameters 303 at a particular elevation and/or during a particular time period. For example, the trend graph 330 can include a horizontal axis and a vertical axis. The horizontal axis can illustrate a specific time or a period of time. For example, the horizontal axis can display the date associated with each of the data points of the user data 302. In some embodiments, the horizontal axis can display the month and/or year associated with each of the data points of the user data 302. In some embodiments, the horizontal axis can display a range of minutes, hours, days, weeks, months, and/or years associated with each of the data points of the user data 302. The user interface 300 can display one or more horizontal axis labels. The horizontal axis labels can include narrow dates associated with a particular data point. The horizontal axis labels can include broader dates, such as a month and/or a year associated with the overall user data displayed in the trend graph 330.

The vertical axis can illustrate a specific elevation at which the user data 302 was monitored, measured, and/or calculated. The intersection between the horizontal and vertical axis can represent sea level in an example. The vertical axis can be incremented at constant elevation intervals. The vertical axis can be incremented at varying elevation intervals. The values of the vertical axis can be displayed in any unit, such as feet or meters, for example. the values of the vertical axis can be displayed in whole numbers in some embodiments. The unit displayed by the user interface 300 in the trend graph 330 can be dependent on a region where the user is located, for example. The unit displayed by the user interface 300 in the trend graph 330 can be dependent on a region set by the user device, for example.

The trend graph 330 can display each value of each data point of the user data 302. In some embodiments, the trend graph 330 can display a range and/or average of values for each time period displayed along the horizontal axis. For example, FIGS. 7A and 7B illustrate an example of the trend graph 330. The trend graph 330 can include one or more data bars 332 and one or more data values. The data bars 332 can be lines. In some embodiments, the data bars 332 can be rectangular and/or cylindrical, among other shapes.

The data values can be a value of each data point, a range of data points, an average of data points over a particular time period, and/or other metric calculated by the system 100 using the values of each data point of the user data 302. FIGS. 7A and 7B illustrate a standard display size of the user interface 300 (for example, without activating the zoom user interface 350). In this configuration, the average of data points over a particular time period can be displayed at an upper end of the data bars 332. When the system 100 receives a request from the user to activate the zoom user interface 350, for example when the user uses one or more zooming gesture methods disclosed herein, the system 100 can display the zoom user interface 350. For example, the user can use zooming gesture methods and/or features, such as a double tap, a finger zoom, and/or a pan, among other gestures. In some embodiments, panning can cause the zoom user interface 350 to have a parallex effect. In such a configuration, a background image, such as a mountain, can move more slowly than the trend graph 330. The parallex effect can advantageously allow the zoom user interface 350 to display the relevant information more clearly.

Figure 8B:
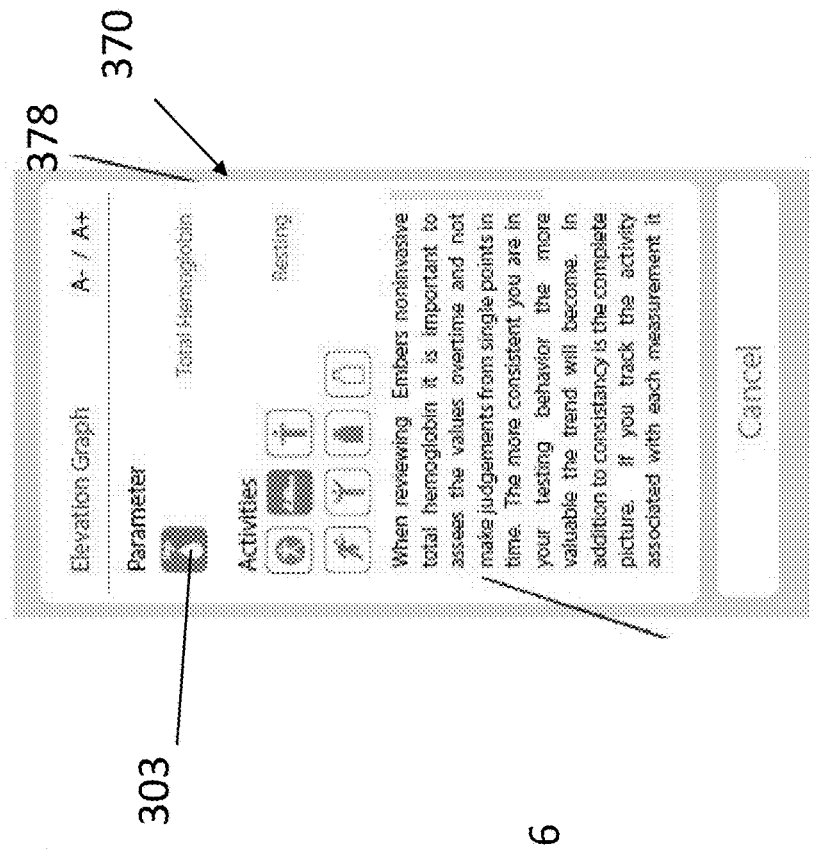
FIGS. 8A-8B depict an example monitoring device user interface illustrated in FIG. 6A.
Figure 8A:
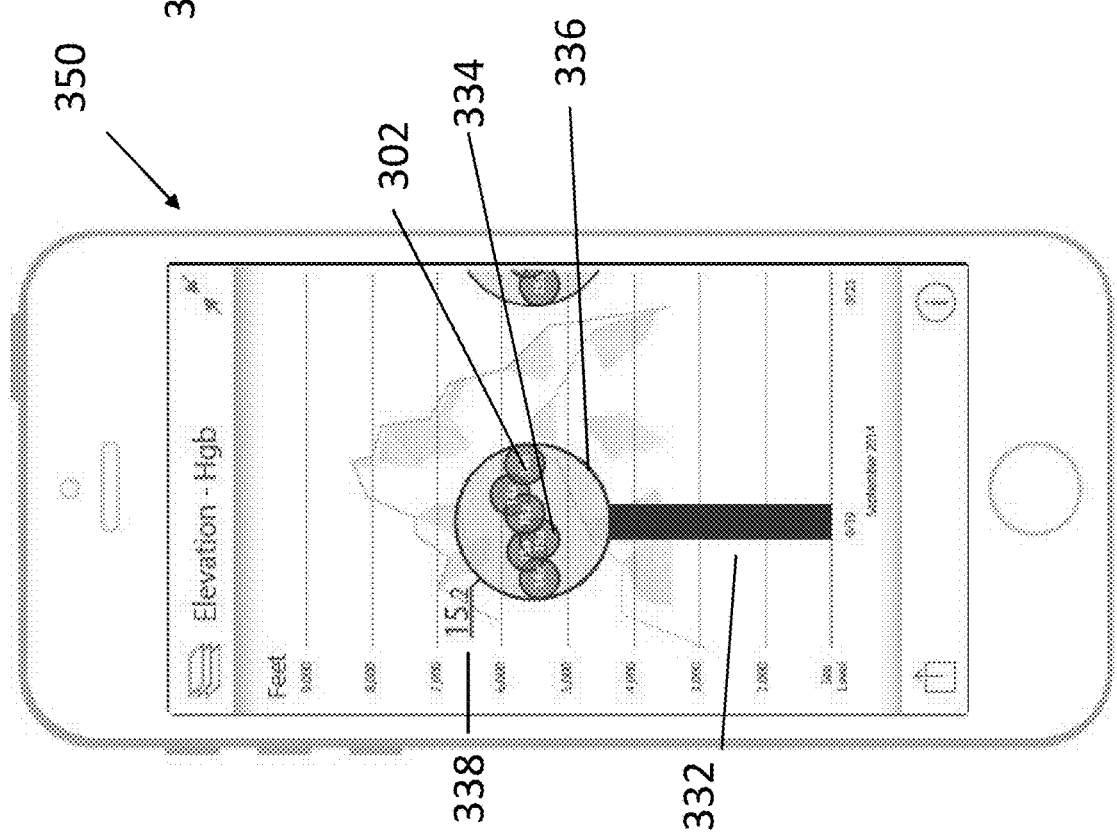
Figure 9B:
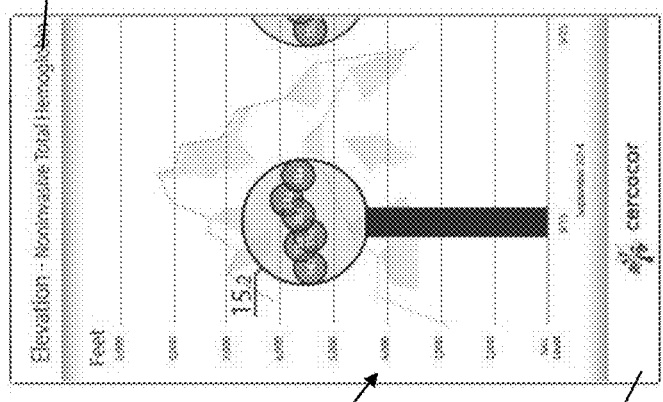
FIGS. 9A-9C depict an example monitoring device user interface illustrated in FIG. 6A.
Figure 9C:
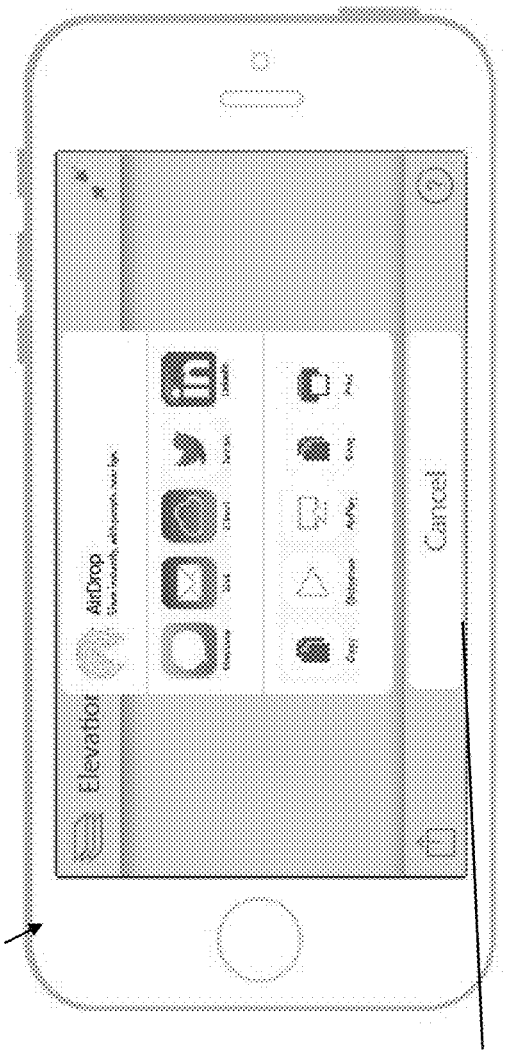
Figure 9A:
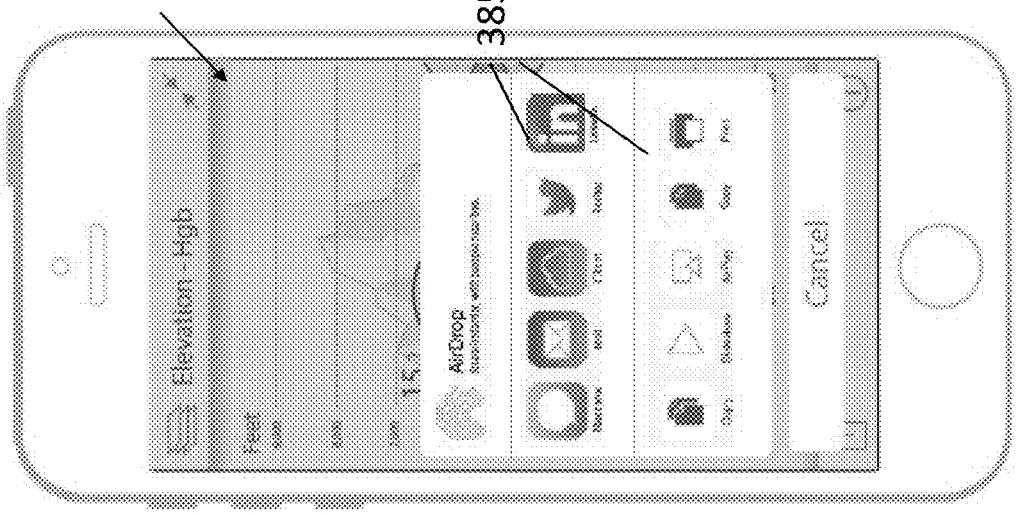

FIG. 8A illustrates an embodiment of the zoom user interface 350. The zoom user interface can display each value of each data point of the user data 302 disposed above the upper end of the data bars 332, for example, rather than an average. In this configuration, each value of each data point that is displayed can represent the value used by the system 100 to calculate a statistic, such as an average value displayed in the user interface 300. This configuration can advantageously allow the user to understand how the system calculated the statistic, such as the average value, displayed in the user interface 300. In some embodiments, the zoom user interface can display the statistic 338 near or adjacent to a group of values of each data point used by the system 100 to calculate the average value. The user interface 300 and zoom user interface 350 can advantageously allow the user to quickly and easily identify what user data is associated with an elevation change. The user interface 300 and zoom user interface 350 can advantageously allow the user to quickly and easily identify when individual data points or statistics calculated based on multiple data points increase as a result of an elevation change.

In some embodiments of the zoom user interface 350, the interface 350 can display the value of each data point in the same configuration as is displayed in the user interface 300 (for example, displayed within a shape 334 and/or with an animation). In some embodiments, to allow the user to more clearly view or access relevant information, the zoom user interface can display the group of values of each data point within a shape 336, as illustrated in FIG. 8A.

In some embodiments, the user interface 300 can be an interactive display. For example, when the user selects the elevation filter, the trend graph 330 can be displayed to the user by the user interface 300. When the trend graph is displayed by the user interface 300, the data bars 332 can dynamically extend upwards from the horizontal axis.

In some embodiments, the value of each data point of the user data 302 can be displayed at an upper end of the data bars 332 in various configurations. For example, as illustrated in FIG. 2A, the data value of each data point is displayed in a shape 334 such as a circle disposed at the upper end of the each data bar 332. The value of each data point can be displayed in a shape, such as a rectangle and/or square, among other shapes. Displaying the value of each data point in the trend graph 330 can allow the user to easily and quickly view and/or access relevant information. In some embodiments, the user interface can highlight the value of each data point in the trend graph 330 to allow the user to view and/or access relevant information more quickly. In some embodiments, when the trend graph 330 is displayed to the user, the shape surrounding the value of each data point and/or the value itself can swell, glow, become enlarged, and/or otherwise be animated to allow the user to view and/or access relevant information more quickly and easily.

Accordingly, the user would be able to quickly determine whether the user has experienced a change in elevation, when the user experienced a change in elevation, and how the change in elevation affected the user's physiological parameters. In some embodiments, the system 100 can automatically determine whether the user has experienced a change in elevation, when the user experienced a change in elevation, and how the change in elevation affected the user's physiological parameters. The user interface 300 can display this information in the elevation graph 330, for example. In some examples, the user interface 300 can display this information in one or more insights 306.

In some embodiments, the value of each data point is not displayed. In some embodiments the trend graph 330 does not include a shape that surrounds the value of each data point. In yet other embodiments, the trend graph 330 does not include any animation that highlights the value of the value of each data point.

FIGS. 11A-11C illustrate examples of the user interface 300 that includes a varying number of data points of the user data 302. As shown in FIGS. 6A-6C, the user interface 300 can display one or more insights 306. The insights 306 can present to the user a general summary of the user data 302.

FIG. 11A illustrates an embodiment of the system 100 wherein no data is available. In this configuration, the user interface 300 can notify the user that no data is available to be displayed. For example, the insights 306 can present to the user that no data is available. In some embodiments, the trend graph 330 can present to the user that no data is available. For example, the trend graph 330 can display no data points of the user data 302. In such a configuration, the trend graph 330 can display text, an image, and/or another indication that no data is available.

FIG. 11B illustrates an embodiment of the user interface 300 wherein one data point 346 has been monitored, measured, and/or calculated by the system 100. In some embodiments, the one data point can be an insufficient amount of user data 302. In some embodiments the one data point can be a sufficient amount of user data 302. However, the system 100 can encourage the user to cause the system to measure, collect, and/or calculate more user data 302. In some configurations, the insight 306 can indicate to the user that an insufficient amount of data has been monitored, measured, and/or calculated by the system 100. In this embodiment, the data point is displayed on the trend graph 330. The data point can be displayed as a single data bar 332 and corresponding data value. As shown in the trend graph 330, the user data 302 can be displayed by the trend graph 330 from left to right.

Some embodiments of the user interface 300 can display more than one data point in the trend graph 330. For example, FIG. 11C illustrates an embodiment of the user interface 300 including at least two data points 346. In some embodiments, at least two data points can be a sufficient amount of user data 302. In such configurations, consecutive data points 346 or groups of data points 346 can be displayed. In some embodiments, consecutive values of the data points can be averaged by the system 100. The user interface 300 can display the average value of the data points in configurations disclosed herein.

In some embodiments, the user interface 300 can include a summary dashboard. The summary dashboard can pop up from the user interface 300, overlap at least a portion of the user interface 300, and/or replace the user interface 300. The summary dashboard can display a summary of the user data 302 displayed in the trend graph 300. The summary dashboard can advantageously provide a summary to the user and/or be shared to third parties and can allow the user to access relevant information more quickly and easily. Accordingly, the summary dashboard can allow the user and/or a third party to help the user achieve enhanced performance by more easily and quickly adjust a diet and/or exercise routine.

In some embodiments, the summary dashboard can include several observations and/or callouts based on the user data 302 displayed in the trend graph 330. For example, the dashboard can display an average, mean, mode, and/or other statistic calculated based on data points representing a particular physiological parameter 303. In some embodiments, the system can determine and/or the summary dashboard can display any of the above-referenced statistics over various time periods, including seven, fifteen, and/or thirty or more days. In some embodiments, the system can determine and/or the summary dashboard can display an elevation the user must travel for one or more of the user's physiological parameters to be affected. In some embodiments, the system can determine and/or the summary dashboard can display the amount of time, for example the number of days, it takes for the user to acclimate to a new baseline at a different elevation. In some embodiments, the system can determine and/or the summary dashboard can display a length of time, for example the number of days, a variation in one or more of the user's physiological parameters lasts.

In some embodiments, the system can determine and/or the summary dashboard can display and/or notify the user of any changes in the user's physiological parameters. In some embodiments, the system can determine and/or the summary dashboard can display and/or notify the user of any particular elevations that affect one or more of the user's physiological parameters based on historical data. In some embodiments, the system can determine and/or the summary dashboard can display and/or notify the user of any particular elevations that affect one or more of the user's physiological parameters based on user data collected in real time. In some embodiments, the system can determine and/or the summary dashboard can display and/or notify the user of any particular elevations that affect one or more of the user's physiological parameters based on a comparison of user data stored in a records database. The records database can be remote from the system 100. In some embodiments, the system 100 can include the records database.

In some embodiments, the system can determine and/or the summary dashboard can display and/or notify the user of any particular elevations that affect one or more of the user's physiological parameters based on a comparison of user data measured during various activities.

In some embodiments, the system can determine and the summary dashboard can display and/or notify the user when a physiological parameter has reached a new high and/or new low. In some embodiments, the system can determine and the summary dashboard can display and/or notify the user when a physiological parameter is not generally optimal. For example, the system can determine and the summary dashboard can display and/or notify the user when any one of the user's physiological parameters is higher than an optimal physiological parameter. In another example, the system can determine and the summary dashboard can display and/or notify the user when any one of the user's physiological parameters is lower than an optimal physiological parameter.

In some embodiments, the system can automatically determine and display the physiological parameters and statistics disclosed herein.

IV. Visual Infographic Yin-Yang Display

FIGS. 12A-12C illustrate an embodiment of the user interface 400. The user interface 400 is similar or identical to the user interfaces 200, 300 discussed above in many respects. Accordingly, numerals used to identify features of the user interfaces 400 are incremented by a factor of one hundred to identify certain similar features of the user interfaces 200, 300. For example, as shown in FIGS. 12A and 12B, the user interface 400 can include a top navigation bar 408, one or more graphs 404, and a bottom navigation bar 412 as described above in connection with the user interfaces 200, 300. The top navigation bar 408 can include a title portion, a subtitle portion, a stretch icon and/or a filter stack icon. In some embodiments, the top navigation bar 408 can include a user profile 424 that can display a name and/or an image selected by the user. The bottom navigation bar 412 can include an information icon and a share icon.

The display information 401 of user interface 400 can include user data 402, such as one or more physiological parameters 403, and one or more graphs 404 as described above in connection with the user interfaces 200, 300. The user interface 400 can include any one, or any combination, of the features of the user interfaces 200, 300. For example, the user interface 400 can be substantially similar to the user interfaces 200, 300. However, in some embodiments the user interface 400 can be displayed in a different configuration than in user interfaces 200, 300.

For example, in the illustrated embodiments, the bottom navigation bar 412 can include a measure icon 414, a history icon 416, a team icon 418, and/or an option icon 420, among other icons. The measure icon 414 can be selected by the user to allow the system 100 to measure the one or more physiological parameters 403. In some embodiments, the user interface 400 can display that a user is measuring the physiological parameters 403. For example, the user interface 400 can display a signal waveform 422 within a widget (described in more detail below). In such configurations, the system 100 can push notifications in real time to the user and/or other users to notify the user and/or other users that a measurement is being taken. In some embodiments, the system 100 can push notifications in predefined intervals. The history icon 416 can be selected by the user to allow the user interface 400 to display a history of user data 402. The team icon 418 can be selected by the user to allow the user interface 400 to display user data of other team members.

The options icon 420 can be selected by the user to allow the user interface 400 to display an options menu.

The user interface 400 can provide a user with an intuitive, easy and/or quick glance assessment of the balance of the user's fitness, goals, and/or wellness. Some embodiments of the user interface 400 can help to increase a user's usage of the user device by influencing the user. For example, FIGS. 12A-12B illustrate an example of the user interface 400. The user interface 400 can influence the user and provide an easily accessible comparison of one or more physiological parameters 403 by providing a plurality of graphs 430. Each graph 430 can correspond to the user and/or other users.

In some embodiments the system can allow a user to more easily understand the balance of the user's fitness and/or athletic value. The system 100 can calculate a metric, such as a numeric value, a physiological parameter, a percentage, a weighted value and/or a ranking. The metric can be calculated by the system 100 using various methods. For example, the system 100 can non-invasively measure one or more physiological parameters using methods disclosed herein. The system 100 can create an index for storing the user data 402, which include the one or more physiological parameters. In some embodiments, the index can represent a comparison of a readiness score, an intensity score, a resting heart rate, a regularity of taking measurements, and/or a frequency of taking measurements, for example. In some embodiments, the index can illustrate a comparison of one or more metrics calculated based on the user data 402 and an intensity score, a resting heart rate, a regularity of taking measurements, and/or a frequency of taking measurements calculated based on another user's user data.

In some embodiments, the user interface 400 can update and display the one or more metrics in real-time. In some embodiments, the user interface 400 can automatically update the one or more metrics at predefined intervals.

Each metric can be calculated using various methods. For example, the system 100 can calculate the readiness score by performing a weighted comparison of directly and indirectly measured values of each data point. The weighted comparison can be calculated by calculating a weighted comparison of a physiological parameter, such as a first of day tHb, a first of day respiration rate, a first of day pulse rate, a previous post workout capital tHb, a first of day SpO2, and/or a heart rate variability, for example, to an average physiological parameter calculated by the system 100 over a selected and/or predetermined period of time. In some embodiments, the weighted comparison can be calculated by comparing the physiological parameter to data collected by a third-party device and/or application, such as sleep and/or activity trackers. Overall, the readiness score can help to provide useful feedback to the user. For example, if the user has a readiness score of 95% calculated based on a consistently low pulse rate, low respiration rate, high tHb, full SpO2, and/or a healthy heart rate variability, for example, the readiness score can indicate to the user that the user is healthy.

In one example, the system 100 can calculate the intensity score by performing a weighted comparison of directly and indirectly measured values of each data point. The weighted comparison can be calculated by calculating a weighted comparison of physiological parameters measured during various activities, such as a post workout heart rate to a pre-workout heart rate, a post-workout SpO2 to a first of day SpO2, a post-workout respiration rate to a pre-workout respiration rate, a pre-workout tHb to a post-workout tHb, and/or third-party data such as bike power (watt-meters), running power (watt-meters), and/or stress scores collected from a third-party application such as activity trackers, for example.

The user interface 400 can display the metric and/or index calculated by the system 100. In some embodiments, the user interface 400 can display a comparison of one or more metrics corresponding to one or more users. For example the one or more metrics can be stored in a database, which can be a remote database. The system 100 can compare the metric between various data points of the user data 402 and user data of other users, such as teammates, friends, and/or celebrities, among other users. The user interface 400 can display the results of this comparison.

FIGS. 12A and 12B illustrate the user interface 400 that can display a plurality of graphs 430. In the illustrated configuration, the graphs 430 display a comparison of an average pulse rate value and an average total hemoglobin value. Each of the plurality of graphs 430 can be displayed by the user interface 400 in a shape of a divided circle, such as a Yin Yang widget. In the illustrated configuration, a first half 432 of the widget represents the average pulse rate value and a second half 434 of the widget represents the average total hemoglobin value. Each of the first half and the second half of the widget can allow the user to easily determine whether the user's metrics are balanced. For example, the graph 430B displayed by user interface 400 can represent a perfect balance. In the illustrated example, each of the first half and the second half of the widget are equal in shape. In some embodiments, the user interface 400 can illustrate unbalanced metrics. For example, graph 430A illustrates an unbalanced user profile. In these configurations the first half 432 and the second half 434 of the widget are not equal in size and shape.

In some embodiments, the user interface 400 can display images 438 associated with each metric displayed in each half of the widget to allow the user to more easily determine what metric is being displayed by the user interface 400. In some embodiments the outer rim 436 of the widget can be used to display certain metrics. For example a color can be displayed by the user interface 400 around at least a portion of the widget to display one or more metrics and/or physiological parameters.

Each of the first and second half 432, 434 of the widget can have at least one flag 440. The at least one flag 440 can be selected by the user. When the user selects the at least one flag, the user can influence another user, such as another team member. For example, when the user selects a first flag 440A of a second user's graph 430A, the system can send a notification the second user to encourage the second user. In some embodiments, when the user selects a second flag 440B of a second user's graph 430A, the system can send a notification to the second user to congratulate the second user. The system can encourage and reward a user's positive behavior by encourage participation between a plurality of users and/or facilitating interaction between a plurality of users. The users can socially reward other users and encourage other users to achieve a well-balanced lifestyle.

In some embodiments, the user interface 400 can display a graph 430B corresponding to a hero, professional athlete, and/or celebrity selected by the user. Accordingly, the user interface 400 can encourage the user to achieve a well-balanced lifestyle and/or enhanced performance by providing an easily accessible comparison to the hero. This can allow the user to more easily compare the balance displayed by the user's graph 430 to a goal balance displayed by the hero's graph 430B.

To view a widget in more detail, the user can select a particular graph 430. In some embodiments, the user can use the various methods for activating a zoom user interface 450, such as the zooming gestures disclosed herein. FIG. 12C illustrates an embodiment of the zoom user interface 450. The zoom user interface 450 can provide more detail and information than the graph 430 displayed in the user interface 400. In some embodiments, the zoom user interface 450 can display values and/or units of each of the metrics corresponding to the first half and the second half of the widget. In some embodiments, the zoom user interface 450 can display labels describing each of the metrics corresponding to the first half and the second half of the widget. In some embodiments, the zoom user interface 450 can display other information, such as a particular elevation at a particular location, a current location of the user, and/or an average elevation, among other relevant information.

V. Terminology

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

Each of the user interfaces shown includes one or more user interface controls that can be selected by a user, for example, using a browser or other application software associated with a patient or clinician device. The user interface controls shown are merely illustrative examples and can be varied in other embodiments. For instance, buttons, icons, dropdown boxes, select boxes, text boxes, check boxes, slider controls, and other user interface controls shown may be substituted with other types of user interface controls that provide the same or similar functionality. Further, user interface controls may be combined or divided into other sets of user interface controls such that similar functionality or the same functionality may be provided with very different looking user interfaces. Moreover, each of the user interface controls may be selected by a user using one or more input options, such as a mouse, touch screen input, or keyboard input, among other user interface input options.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A system configured to assist a user in improving physiological performance during exercise by monitoring total hemoglobin measurements over a range of circumstances and providing user data in a useful way for user use, the system comprising:
   a non-invasive physiological sensor and hardware processor configured to obtain user physiological data and elevation data over a period of time, wherein the user data comprises a plurality of total hemoglobin measurements obtained at a plurality of elevations relative to sea level;
   a database configured to store the user data; and
   a user interface generated by a system having one or more hardware processors and one or more servers, wherein the user interface is configured to display a first total hemoglobin measurement of the plurality of total hemoglobin measurements, and provide in a graphical presentation, an indication of the first total hemoglobin measurement according to changes in elevation relative to sea level, wherein the first total hemoglobin measurement is provided according to an elevation relative to sea level at which it was obtained, and wherein the user interface is configured to display an image representing the first total hemoglobin measurement, and
   wherein the user interface is configured to receive a selection by a user of the plurality of total hemoglobin measurements.

2. The system of claim 1, wherein the user interface is configured to display a second total hemoglobin measurement of the plurality of total hemoglobin measurements and provide an indication of the second total hemoglobin measurement at an elevation relative to sea level at which it was obtained.

3. The system of claim 1, wherein the non-invasive physiological sensor comprises: a plurality of emitters configured to emit light; and one or more detectors configured to detect light attenuated by a tissue site of the user.

4. The system of claim 1, wherein the non-invasive physiological sensor comprises a reusable sensor configured to clip onto a tissue site of the user.

5. The system of claim 1, wherein the selection by the user comprises a subset of the plurality of total hemoglobin measurements obtained by the non-invasive sensor during a period of time.

6. The system of claim 1 wherein the selection by the user comprises a subset of the plurality of total hemoglobin measurements obtained by the non-invasive sensor at a range of elevations relative to sea level.

7. The system of claim 1, wherein the selection by the user comprises a subset of the plurality of total hemoglobin measurements obtained by the non-invasive sensor during a selected activity.

8. The system of claim 1, wherein the user interface is configured to display an indication of suboptimal total hemoglobin measurement according to an elevation relative to sea level.

9. The system of claim 1, wherein the graphical presentation comprises a data bar extending upwards from a horizontal axis.

10. The system of claim 9, wherein the data bar comprises a line.

* * * * *